(12) United States Patent
Pacheco

(10) Patent No.: US 10,974,018 B2
(45) Date of Patent: Apr. 13, 2021

(54) THERAPEUTIC BLANKET

(71) Applicant: CapeAble Sensory Products, LLC, Winona Lake, IN (US)

(72) Inventor: Marna G. Pacheco, Winona Lake, IN (US)

(73) Assignee: CapeAble Sensory Products, LLC, Winona Lake, IN (US)

(*) Notice: Subject to any disclaimer, the term of this patent is extended or adjusted under 35 U.S.C. 154(b) by 0 days.

(21) Appl. No.: 16/845,545

(22) Filed: Apr. 10, 2020

(65) Prior Publication Data

US 2020/0238045 A1 Jul. 30, 2020

Related U.S. Application Data

(63) Continuation-in-part of application No. 15/701,762, filed on Sep. 12, 2017, now Pat. No. 10,617,158, which is a continuation-in-part of application No. 14/693,958, filed on Apr. 23, 2015, now abandoned.

(60) Provisional application No. 62/001,445, filed on May 21, 2014.

(51) Int. Cl.
| | |
|---|---|
| A47G 9/02 | (2006.01) |
| A61M 21/00 | (2006.01) |
| A61M 21/02 | (2006.01) |
| A47G 9/00 | (2006.01) |

(52) U.S. Cl.
CPC .............. *A61M 21/00* (2013.01); *A47G 9/007* (2013.01); *A47G 9/0223* (2013.01); *A61M 21/02* (2013.01); *A61M 2021/0022* (2013.01); *A61M 2205/0205* (2013.01)

(58) Field of Classification Search
CPC ...... A47G 9/02; A47G 9/0207; A47G 9/0223; A61M 21/00
USPC ..................................... 5/482, 485, 500, 502
See application file for complete search history.

(56) References Cited

U.S. PATENT DOCUMENTS

| | | | |
|---|---|---|---|
| 1,365,731 A | * | 1/1921 | Schloss ................... A41F 17/00 2/273 |
| 2,042,442 A | | 5/1936 | Buchman |
| 4,330,982 A | | 5/1982 | Vissers et al. |
| 4,689,844 A | | 9/1987 | Alivizatos |
| 4,839,934 A | * | 6/1989 | Rojas ................... A47G 9/0207 5/485 |
| 5,606,746 A | | 3/1997 | Shelton et al. |
| 6,383,130 B1 | | 5/2002 | Wade et al. |
| 6,665,879 B2 | | 12/2003 | VandenBerg |
| 7,010,814 B2 | | 3/2006 | Benziger |
| 7,178,185 B1 | | 2/2007 | Nattler |
| 7,870,623 B2 | | 1/2011 | Judd |
| 2007/0028387 A1 | | 2/2007 | Mathis |

(Continued)

OTHER PUBLICATIONS

"Calming Effects of Deep Touch Pressure in Patients with Autistic Disorder; College Students, and Animals", Temple Grandin, Ph.D., Journal of Child and Adolescent Psychopharmacology, vol. 2, No. 1, 1992 (11 pages).

*Primary Examiner* — Fredrick C Conley

(74) *Attorney, Agent, or Firm* — Taylor IP, P.C.

(57) ABSTRACT

A therapeutic blanket including first and second outer layers that are attached together, and an internal matrix of generally equal sized cells. Each cell containing a measured weighted mass, the mass being held within the respective cell. The matrix being secured to the first and second outer layers along an outer perimeter of the blanket.

17 Claims, 15 Drawing Sheets

(56) References Cited

U.S. PATENT DOCUMENTS

2011/0047698 A1* 3/2011 Parker .................. A47G 9/0207
5/502
2014/0259423 A1 9/2014 Falck

* cited by examiner

# THERAPEUTIC BLANKET

CROSS REFERENCE TO RELATED APPLICATIONS

This is a continuation-in-part application based upon U.S. non-provisional patent application Ser. No. 15/701,762 entitled "THERAPEUTIC FABRIC ARTICLE", filed Sep. 12, 2017, which is incorporated herein by reference. Application Ser. No. 15/701,762 is a continuation-in-part application based upon U.S. non-provisional patent application Ser. No. 14/693,958 entitled "THERAPEUTIC FABRIC ARTICLE", filed Apr. 23, 2015, which is incorporated herein by reference. Application Ser. No. 14/693,958 was based upon U.S. provisional patent application Ser. No. 62/001,445 entitled "THERAPEUTIC FABRIC ARTICLE", filed May 21, 2014.

BACKGROUND OF THE INVENTION

1. Field of the Invention

The present invention relates to a therapeutic blanket, and, more particularly, to weighted therapeutic blankets.

2. Description of the Related Art

The tactile system provides input to the brain for interpretation of various types of touch, pressure, temperature and pain through receptors in the skin. For example, deep pressure touch can be very calming. This type of input facilitates the release of dopamine, also known as the "pleasure chemical", in the brain that helps people maintain emotional neutrality. Dopamine activates the parasympathetic nervous system for a relaxed, neutral and balanced homeostatic state. Dopamine may neutralize cortisol and adrenaline, which contribute to the fight or flight response of the autonomic nervous system. Conversely, an excess of dopamine may increase hyperactivity, which may then be regulated by increasing serotonin levels via the proprioceptive system. Proprioception refers to the information gathered by the nervous system from one's muscles, joints, tendons and ligaments. It is also known as the "position sense", which offers a sense of grounding that is interpreted by the emotional state as perceived security and/or safety. Proprioceptive input facilitates the release of serotonin, the master regulator of the central nervous system (brain and spinal cord), as well as dopamine. Valued as the "coping chemical", serotonin breaks up dopamine thereby preventing hyperactivity and over-processing of information, resulting in a neutral state of arousal. Persons having difficulty processing information from one or both of these systems will demonstrate behaviors that impede function. Poor sensory modulation leads to a compromised body system that is interpreted by the central nervous system as being "in pieces". The brain and the body will focus on keeping the individual's self together, thereby rendering the individual substantially incapable of efficient higher cortical function. The basic sub-cortical needs must first be met before focus can be diverted to higher cortical function. Maintaining the nervous system at a calm and alert state is imperative for cognitive functions and learning.

Persons affected by impaired function of the nervous system can include those with developmental disabilities, Sensory Processing Disorders (SPD), Attention Deficit Hyperactivity Disorders (ADHD), Post Traumatic Stress Disorder (PTSD) and autism spectrum disorders. Individuals with these conditions have difficulty maintaining homeostasis within the nervous system, thereby inhibiting their ability to participate in effective learning and sometimes causing behaviors incongruent with social norms. Such identifiable behaviors can include constant movement, impulsivity, decreased attention span, inability to focus on a particular task and seeking of heavy-pressure related tasks.

Current treatments for persons affected by an impaired function of the nervous system can include pharmaceutical products, behavioral therapy, speech-language therapy, physical therapy, play-based therapy, situational therapy and nutritional therapy. Often in combination, these forms of treatment can be a tremendous benefit; yet, they are not without their own shortcomings. For instance, pharmaceuticals may elicit irresponsive results, or worse they may cause adverse side effects for a particular individual. Results from treatment in general can vary greatly from one individual to another. Therefore, partially due to the individualistic nature of conventional treatment methods, alternative additional forms of treatment were developed, including types of treatments utilizing deep pressure and tactile input therapy.

Some applications of deep pressure therapy in the prior art include use of squeeze machines, weighted blankets, and various weighted articles such as gloves or vests. These deep pressure devices have been known to release serotonin, which helps an individual feel calm and secure. However, the problem with many of these forms of deep pressure therapy is that they are restrictive and can keep the user from fully engaging in daily activities such as routine tasks, learning, common social interactions and play.

What is needed in the art is therapeutic blanket that serves a dual sensory function with reference to the proprioception and tactile systems in a healthcare environment.

SUMMARY OF THE INVENTION

The present invention relates to a weighted therapeutic blanket that may be made of layers of cloth or fabric with specific distributions of weighted elements.

The present invention provides therapeutic blankets, which are configured to serve a dual sensory function with reference to the proprioception and tactile systems. While the present invention is beneficial in home, school and community settings, it is primarily directed for use in medical and therapy settings, for example, but not limited to: therapeutic institutional mental health settings and inpatient and outpatient medical surgery and treatment settings. The present invention is beneficial for treatments throughout the lifespan, from birth through hospice care, of persons either having neurological disabilities or being neurologically typical (NT) but demonstrating anxiety and related conditions. More specifically, the garment according to the present invention is a discreet and aesthetically pleasing intervention aimed at the neurological/sensory underpinnings contributing to unacceptable sensory-seeking behaviors in children and adults with disabilities, and neurologically typical individuals with situational anxiety.

The invention in one form is directed to a therapeutic blanket including first and second outer layers that are attached together, and an internal matrix of generally equal sized cells. Each cell containing a measured weighted mass, the mass being held within the respective cell. The matrix being secured to the first and second outer layers along an outer perimeter of the blanket.

The invention in another form is directed to a therapeutic blanket including a plurality of weighted fabric chains, a bladder, and top and bottom fabric layers. The bladder has a plurality of channels therein, with a corresponding one of the fabric chains being inserted into each of the channels. The bladder is secured between the top fabric layer and the bottom fabric layer along an outer perimeter of the fabric layers.

BRIEF DESCRIPTION OF THE DRAWINGS

The above-mentioned and other features and advantages of this invention, and the manner of attaining them, will become more apparent and the invention will be better understood by reference to the following description of embodiments of the invention taken in conjunction with the accompanying drawings, wherein.

Corresponding reference characters indicate corresponding parts throughout the several views. The exemplifications set out herein illustrate embodiments of the invention and such exemplifications are not to be construed as limiting the scope of the invention in any manner.

DETAILED DESCRIPTION OF THE INVENTION

Figure 1:
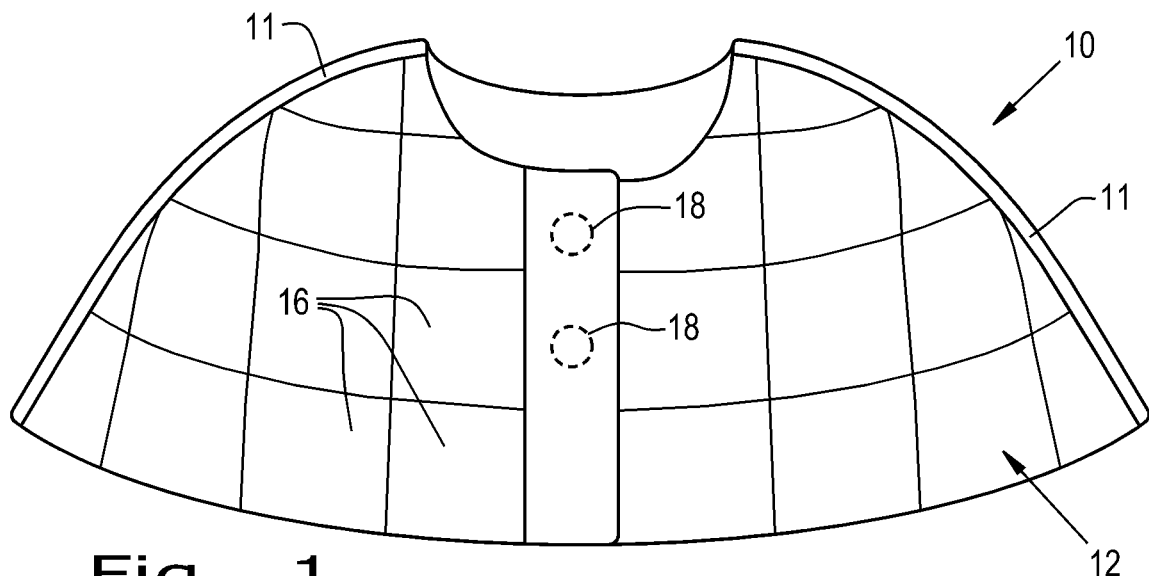
FIG. 1 is a front view of an embodiment of the inventive garment.
Figure 2:
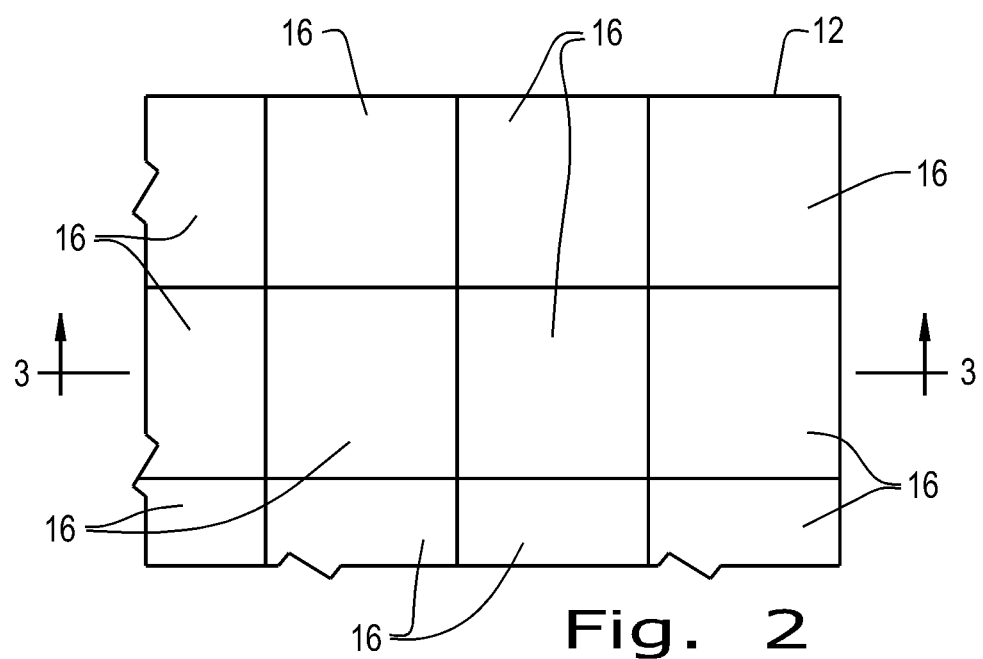
FIG. 2 is a diagram that illustrates the fabric pattern of the inventive garment.
Figure 3:
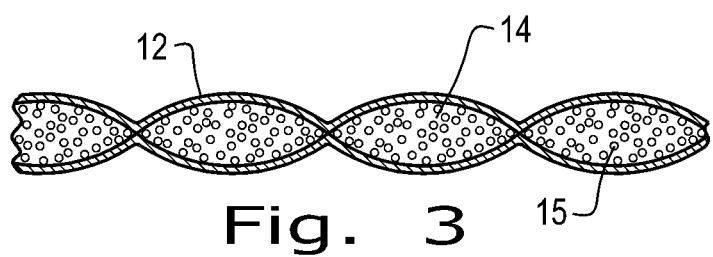
FIG. 3 is a diagram that illustrates the distribution of a weighted material inside the fabric shell of the inventive garment.

Referring now to the drawings, and more particularly to FIGS. 1-3, there is shown an embodiment of the inventive garment 10, which is generally constructed of a fabric shell 12 that has a quilted pattern in the form of a plurality of quilted squares 16 for securing a weighted filling 14 therein. The garment 10 further includes a pair of curved shoulder panels 11 and at least one fastener 18.

The garment 10 is generally configured such that there is a substantially even weight distribution within the quilted squares 16 from an anterior side, shown in FIG. 1, to a posterior side (not shown) of the garment 10. According to the embodiment shown in FIG. 1, the garment 10 encompasses the shoulder girdles of a wearer, and it has a contour in the likeness of a shoulder cape. The curved shoulder panels 11 allow a clear, defined fit, which in combination with the elastic character of the fabric shell 12 maintains the placement of the garment 10 without inhibiting functional upper-body use of the wearer. Additionally, due to the snug fit of the garment 10 around the shoulder girdle, there is a greater surface contact area for sensory input. This design ensures accurate and consistent pressure to the body via the peripheral nervous system. This even weight distribution provides necessary input to the surface area of the mid chest region, shoulder girdle (both anterior and posterior) and upper back region. Further, the dermatomes are activated with constant and repeated stimulus each time the garment is applied or worn while providing the user with a secure fit that provides a "hugging" or compression fit of comfort.

Fabric shell 12 of the present embodiment is a plush material with a slight elasticity, which adds both to the tactile and proprioceptive benefit of the garment 10, while providing a comfortable compression fit. The fabric shell 12 houses the weighted filling 14, which can be in the form of a glass or polymer pellet filling 15 as in the present embodiment, or in the form of any other suitable filling that is durable and washable. The fabric shell 12 of the present embodiment has a quilted pattern in the form of a plurality of quilted squares 16. However, the fabric shell 12 may have any geometric pattern that equally distributes the weighted filling 14 throughout the garment 10, including a quilted triangular pattern or a diamond pattern. Each quilted square 16 is designed to be substantially the same size and to contain substantially the same amount of the weighted filling 14. In the embodiment shown in FIG. 1, each quilted square 16 is 2½ square inches; however, the size of each quilted square 16 is not limited to 2½ square inches. The quilted squares 16 could be sized in a range from 1 to 3 square inches. Further, the quilted geometric pattern may be comprised of various shapes that are not of equal size.

The fastener 18 is positioned at the anterior side of the garment 10 such that the wearer can easily don and doff the garment 10. The embodiment shown in FIG. 1 has a fastener 18 in the form of two magnetic fasteners (not shown). Additional possible fasteners include buttons, snaps, clasps, laces, Velcro® or any other suitable fastener for securing the garment about the body of the user. Magnetic fasteners provide simplicity in fastening and they eliminate the potential for startling the wearer due to a sudden auditory stimulus, as would snaps or hook and loop fasteners. Additionally, magnetic fasteners allow for the garment 10 to be readily reversible. The magnetic fasteners are housed within the fabric shell 12, in other words they are sewn into the interior of the garment 10, and they do not extend to the exterior of the garment 10. Therefore, the wearer's temptation to fidget with the fastener 18 in the present embodiment is reduced, allowing the wearer to more easily focus on the task at hand.

Figure 4:
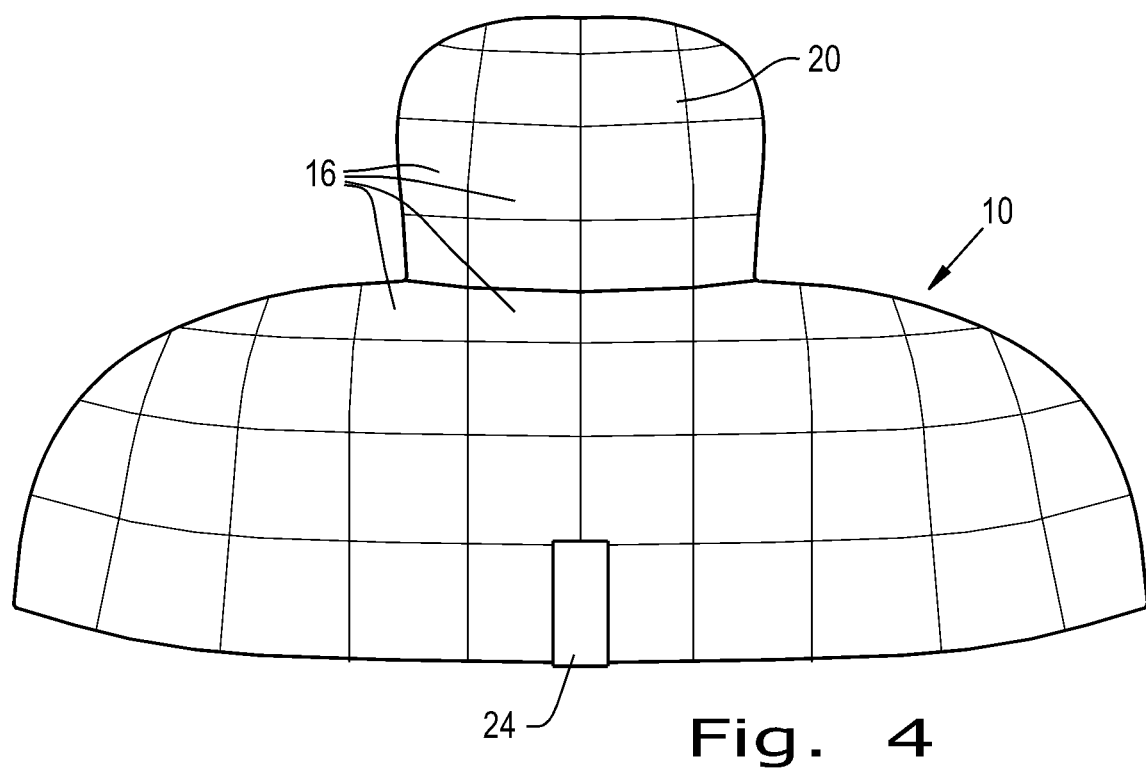
FIG. 4 is a posterior view that illustrates an integrated hood attached to the embodiment shown in FIG. 1.

Referring now to FIG. 4, the garment 10 may further include an integrated hood 20, which also is constructed of the same plush fabric shell 12 shown in FIG. 3. The integrated hood 20 includes the weighted filling 14, which is substantially evenly distributed throughout the fabric shell 12 of the hood 20. The integrated hood 20 provides an additional dimension of sensory input, while maintaining the quilted configuration and cohesive appearance. It is also feasible for the integrated hood 20 to be formed as a separate unit, which can be coupled with the garment 10 by using an additional fastener or a set of additional fasteners (not shown). The additional fasteners may be in the form of magnetics, buttons, snaps, clasps, Velcro® or any other fastener capable of securing the garment 10 to the hood 20.

Additionally, as illustrated in FIG. 4, a loop 24 may be provided on the posterior, bottom edge of the garment. This facilitates a greater sense of independence because when the integrated hood 20 is not in use the wearer can easily hang it in his or her "cubby", locker at school, or on a hook in a social atmosphere or at home.

Figure 5:
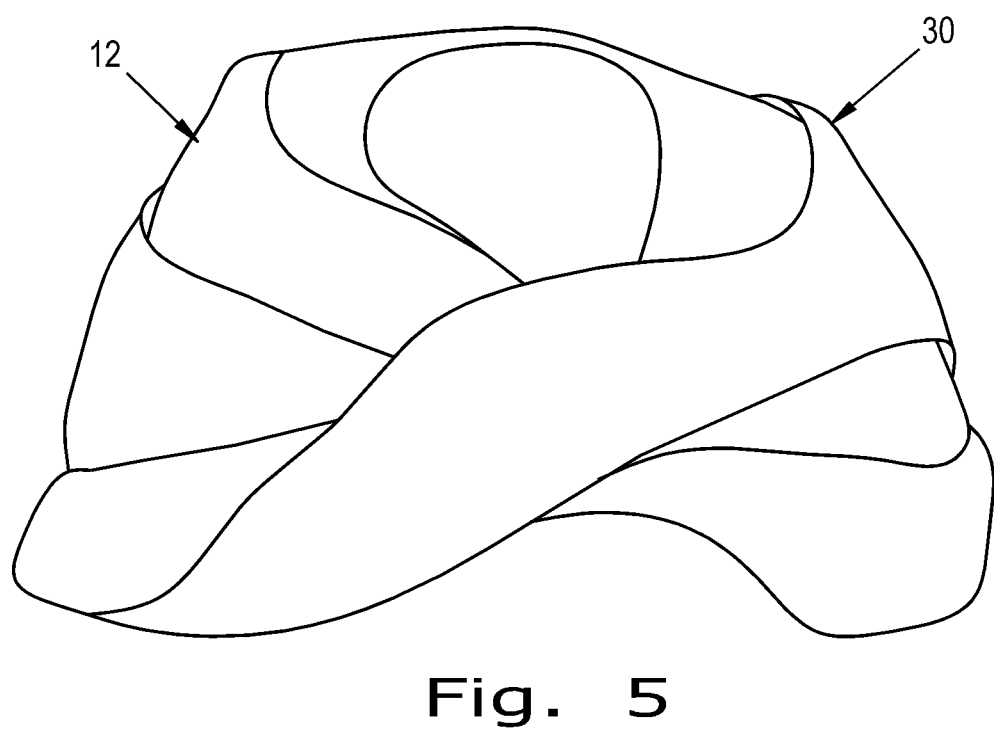
FIG. 5 is a front view of a second embodiment of the inventive garment, which is in the form of an endless loop of fabric.

Referring now to FIG. 5, there is shown a second embodiment of the inventive garment 10 according to the present invention in the form of an endless loop of fabric 30, which may be draped about the head, shoulders and neck of the wearer. Garment 30 includes the fabric shell 12, shown in FIG. 3, which is constructed with a plurality of quilted squares 16, as illustrated in FIG. 2. The quilted squares 16 include a weighted filling 14, which can be in the form of a plurality of glass or polymer pellets (not shown) therein. According to this second embodiment of the present invention, the weight of the weighted material 14 is distributed substantially evenly across the entirety of the garment 30.

Figure 6:
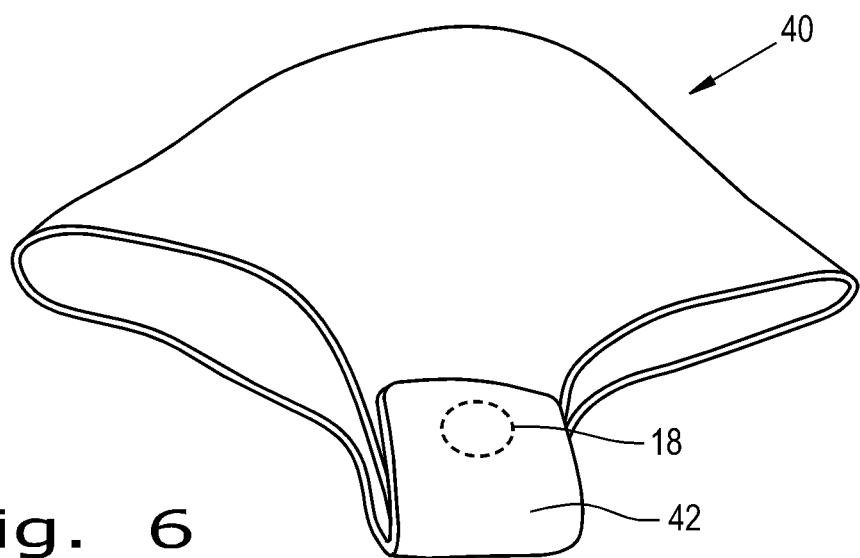
FIG. 6 is a side perspective view that illustrates a third embodiment of the inventive garment in the form of a stand-alone hood.

Referring now to FIG. 6, a third embodiment of the inventive garment is provided in the form of a stand-alone hood 40. The hood 40 includes a chinstrap 42 and at least one fastener 18. Hood 40 provides proprioceptive input at the crown of the head of a user, via even disbursement of weight to the frontal and parietal portions of the cranium. The chinstrap 42 is configured for applying a predetermined amount of pressure to the temporomandibular joint (TMJ) when the chinstrap 42 is fastened under the chin of a user. The TMJ is a site for sensory stimulation and organization. A pressure input by the chinstrap 42 advantageously reduces the quantity and intensity of maladaptive oral habits, for example, excessive mouthing, teeth grinding and chewing on clothing and/or fingers. The fastener 18 can include magnets, buttons, snaps, clasps, laces, Velcro® or any other suitable fastener for securing the chinstrap 42. Exemplary uses for the stand-alone hood 40 may include: (1) Use in transition prior to getting a child's hair cut; (2) Calming an otherwise over-stimulated child in a loud, bright community setting, such as a grocery store, department store or restaurant; (3) Minimizing environmental input (i.e., light, noise and movement of peers) from the classroom in a school setting; and (4) Calming an overwhelmed child in a social setting with a number of different people and activities going on around the user.

Figure 7:
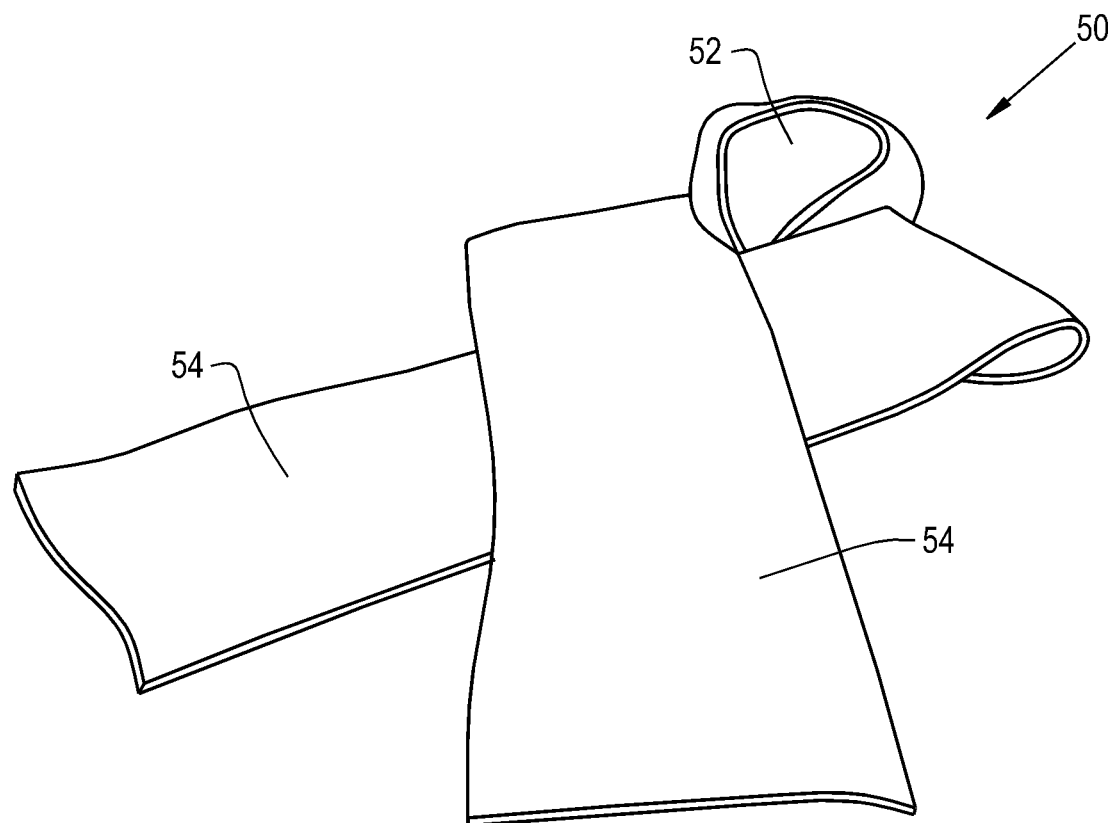
FIG. 7 is a perspective view that illustrates a fourth embodiment of the inventive garment in the form of a hooded wrap garment.

Referring now to FIG. 7, there is shown a fourth embodiment of the present invention in the form of a hooded wrap garment 50, constructed of the same fabric shell 12 described above and having an even distribution of the weighted filling 14. The weighted filling 14 can be, for example, a glass or polymer pellet filling (not shown) encapsulated within the fabric shell 12 for even weight distribution across the area of the garment 50. The garment 50 further includes a hood portion 52 and a pair of symmetrical, elongate structural members 54 that extend outwardly from the hood portion 52. The extended length of the elongate structural members 54 provides additional versatility in how the hooded warp garment 50 is worn because the elongate structural members 54 can be extended up to 4 or more feet (ft.). For example, depending upon the input desired, the length of the hooded wrap garment 50 may be wrapped or draped unilaterally or bilaterally over the shoulders of the user, or may be draped comfortably on the lap or about the waist of the wearer when in a seated or reclining position. Upon standing, the hooded wrap garment 50 is configured to drape downwardly to the top of the knees of a wearer, thereby eliciting a greater pressure input through the shoulders as is promoted by gravitational effects. Advantageously, the hooded wrap garment 50 provides flexibility in use and directed input to the proprioceptive and tactile sensory systems.

The hooded wrap garment 50 according to the present invention may also be configured without the hood portion as a simple wrap or scarf (not shown). Such a wrap or scarf can be wrapped over one or both shoulders, or it may be draped about the neck of the user to extend down the back or the front of the body. Reverse wear of such a wrap or scarf, in other words with opposing ends extending down the back of the wearer, would elicit a calming sense due to the selected proprioceptive and tactile input on the user's nervous system via providing substantially uniform weight distribution across the chest and the sternum.

Figure 8:
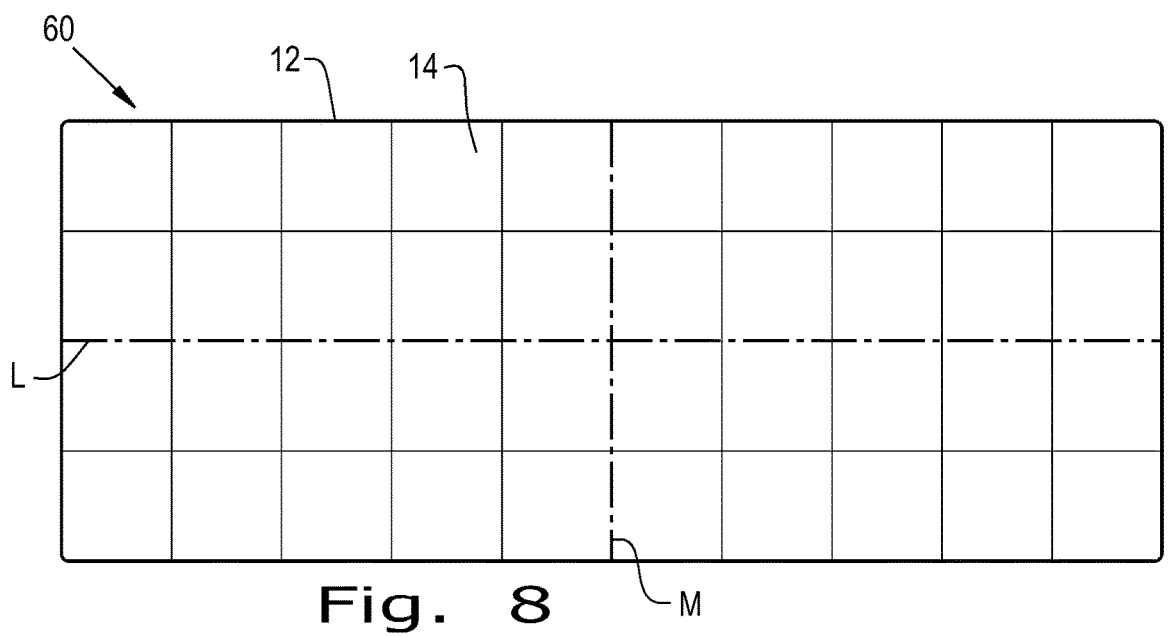
FIG. 8 illustrates a fifth embodiment of the present invention in the form of a lap pad.

Referring now to FIG. 8, there is shown a fifth embodiment of the present invention configured as a lap pad 60. The lap pad 60 is formed of the same plush, quilted fabric shell 12 with the weighted filling 14 therein, which is substantially evenly distributed across the area of the lap pad 60 for maximum proprioceptive input. The lap pad 60 may be used simply as a weighted lap pad or folded in half to increase the weight distribution over a smaller area, for example, at the center of the lap of a user. Additionally or alternatively, the lap pad 60 may be utilized as a muff when a user's hands are placed between the layers of the folded lap pad 60, offering additional proprioceptive and tactile input to the hands, thereby calming the user. Also, by positioning the hands of a user within the folds of the lap pad 60, the upper extremity tremoring of a user may be dampened, thereby soothing the user through the enhanced proprioceptive and tactile inputs on the nervous system.

Optionally, a plurality of magnetic fasteners (not shown) may be provided at the corners of the lap pad 60, affixed within the fabric shell 12. This would allow the user to secure the lap pad 60 along a longitudinal axis L or a lateral axis M for increased versatility in use, as shown in FIG. 8. For example, the lap pad 60 may be secured around the neck of a user for targeted proprioceptive and tactile input to the neck and/or shoulders for a more proximal proprioceptive experience. Alternatively, the lap pad 60 may be worn around the hips as a belt for proximal stability and input at the pelvic girdle. This is particularly advantageous for providing body-awareness for ambulation and gait training.

Figure 9:
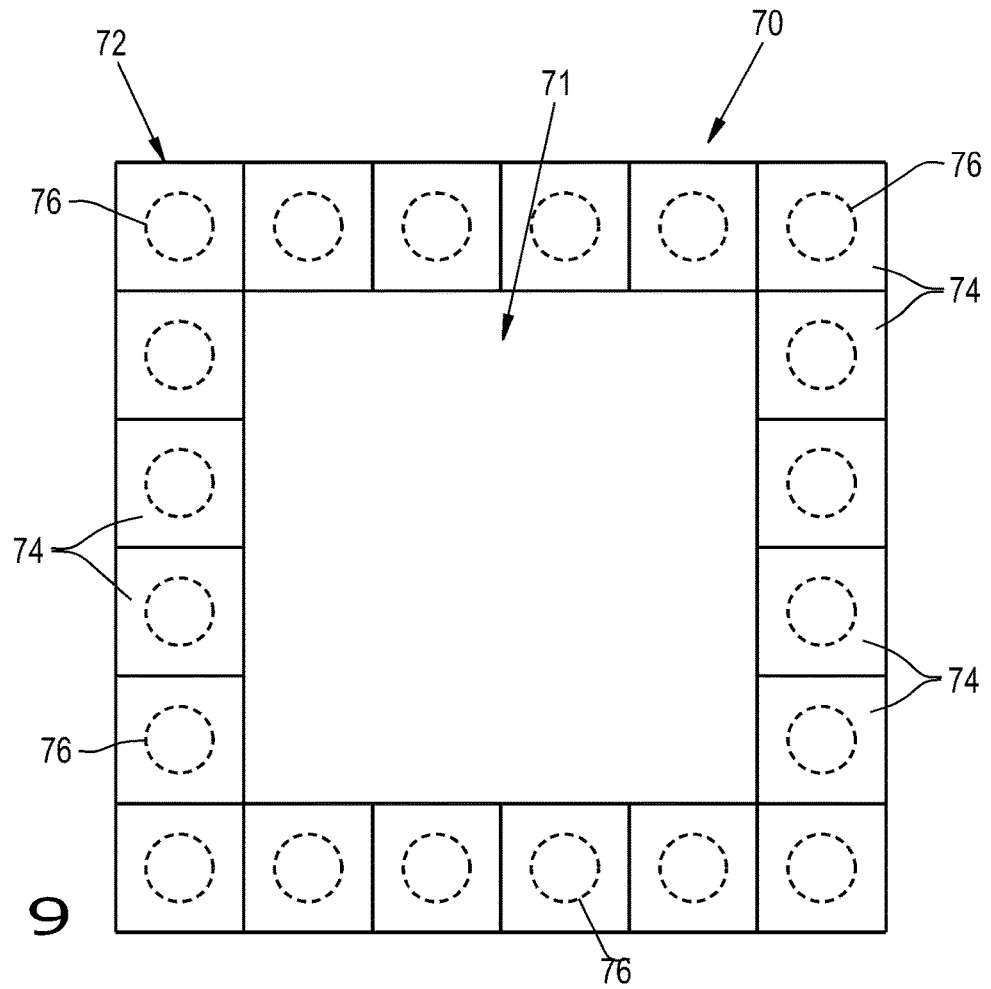
FIG. 9 is a diagram that illustrates a sixth embodiment of the inventive garment in the form of a perimeter blanket.

Referring now to FIG. 9, a sixth embodiment of the present invention provides a perimeter blanket 70, which includes a central panel 71 and a perimeter area 72 formed by the fabric shell 12, which is illustrated in FIG. 3. The perimeter area 72 further includes a plurality of quilted squares 74 that house the weighted filling 14, which is substantially uniformly distributed throughout the fabric shell 12. Perimeter area 72 outlines the central panel 71, which is also formed of the same plush fabric as perimeter area 72, for a calming input into the tactile sensory system. Advantageously, since the quilted squares 74 are positioned about the perimeter it allows the user to selectively distribute the weight to provide a desired amount of pressure and tension across selected areas of the body, thereby allowing the user to define the desired proprioceptive input into the nervous system. The perimeter blanket 70 thereby provides both weight and compression when draped and/or wrapped about the body with varying degrees of tension. Further, because of the unique design and weight distribution, the perimeter blanket 70 will not shift off of a user's lap or body, despite active movement.

The perimeter blanket 70 may further optionally include, encased within the fabric shell 12, a plurality of magnetic inserts 76 having respective alternating polarities positioned around the periphery of the perimeter blanket 70 such it may be gathered up into a sack or a bag for a variety of uses.

Figure 10:
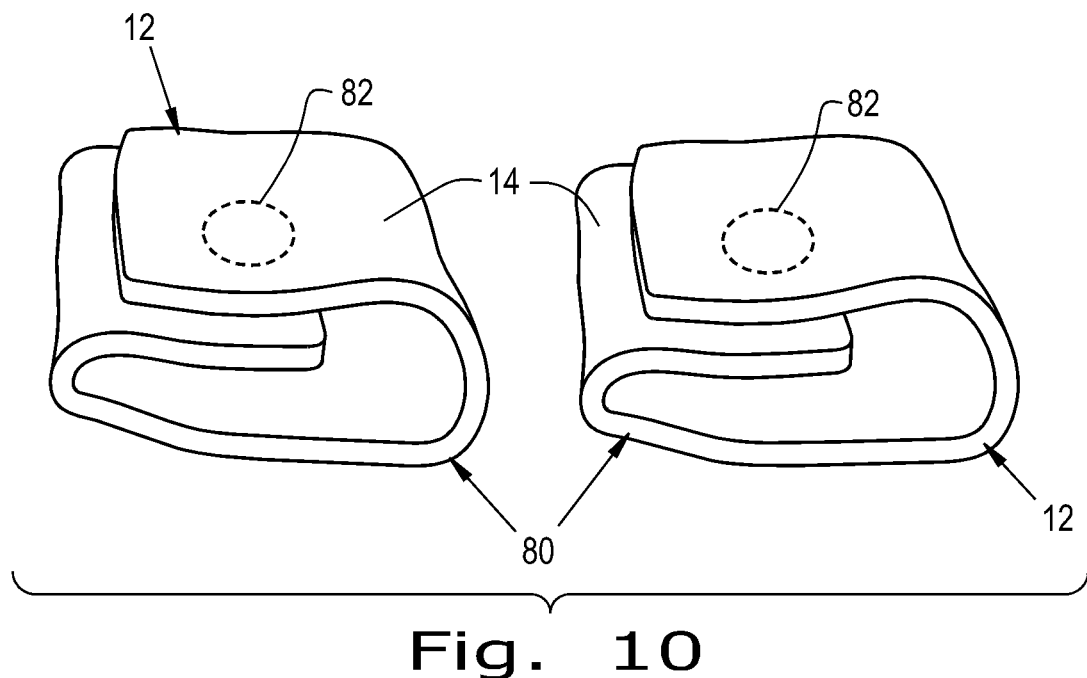
FIG. 10 is a perspective view that illustrates a seventh embodiment of the inventive garment in the form of proprioceptive and tactile input bands.

Referring now to FIG. 10, there is shown a seventh embodiment in the form of proprioceptive and tactile input bands 80, which may be positioned about the wrists or ankles of a user. The bands 80 include the plush fabric shell 12, the weighted filling 14 and a fastener configured as a plurality of magnets 82. Provided in varying widths and lengths, the bands 80 offer proprioceptive input for a number of functional activities, for example, handwriting and fine-motor activities when positioned about the wrists. The magnets 82 are hidden within the fabric shell 12 and are positioned at opposing ends within contiguous quilted squares (not shown), such that bands 80 may be folded lengthwise for a greater intensity of weight distribution. The plush fabric shell 12 has a slight elasticity that offers an additional sensory component of compression, depending upon the tension applied to bands 80 in positioning them about the body.

Figure 11:
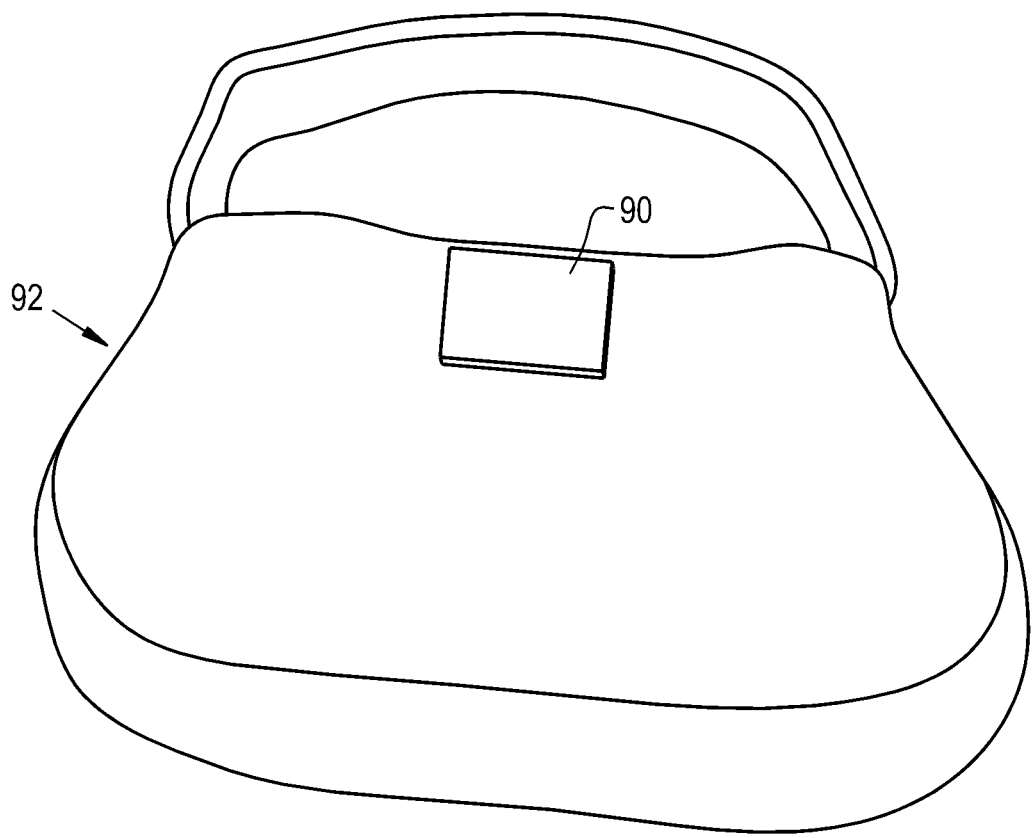
FIG. 11 illustrates an additional accessory of the present invention in the form of a normalized and fashionable purse.

According to the present invention, additional optional accessories may be utilized in association with any of the above-referenced embodiments of the present invention. For example, magnetic patches 90 (see FIG. 11) may be secured to any of the above-identified embodiments using a fastener 18. Such magnetic patches 90 may be used to provide visual or tangible recognition of tasks accomplished throughout the user's day. These tasks may include visual presentations of information such as emotional status, functional prompts for visual sequencing, self-help and/or daily skills and routines, sports, therapy sessions, etc.

Also, an additional accessory in the form of a purse 92 (see FIG. 11), bag or backpack (not shown) may be provided in a matching fabric pattern to be utilized in association with the above-identified inventive garments, thereby providing an aesthetically pleasing, socially acceptable or normalized and fashionable set, while also meeting the specialized neurologic needs of the user. Selective weighting of the purse 92, bag or backpack may be provided such that the fashionable accessory can be converted for purposes of selective proprioceptive input at predetermined points across and around the user's body. The purse 92, bag or backpack may also be provided with overlapping magnets (not shown) on the straps to offer a safety release feature.

Figure 12:
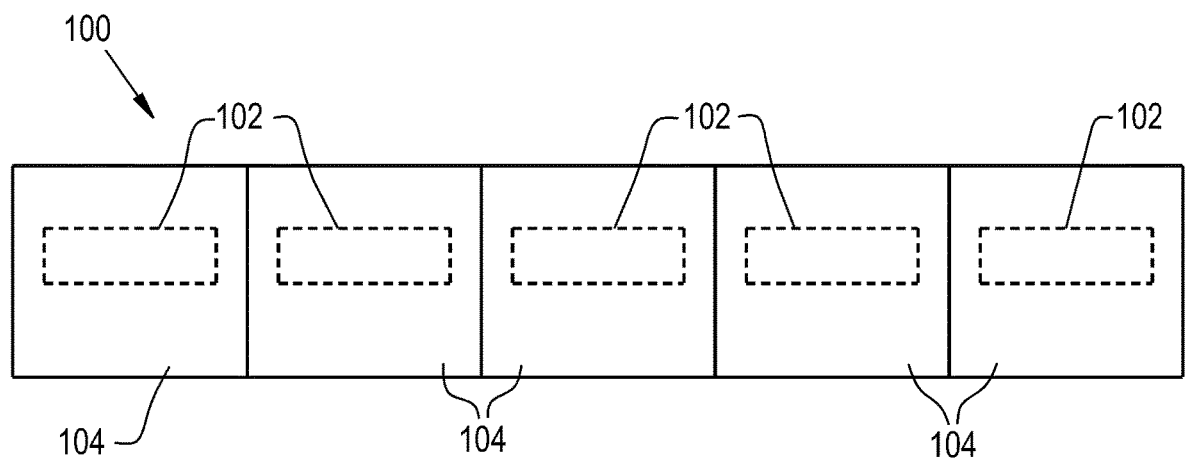
FIG. 12 is a diagram that illustrates another additional accessory of the present invention in the form of a therapeutic fidget.

Referring to FIG. 12, another accessory is shown as an inventive therapeutic fidget 100. The fidget 100 includes a plurality of square linear magnets 102 positioned within a plurality of quilted fabric squares 104, which aid in self-regulation of a user to calm and organize the nervous system. By actively grasping and pulling the magnetic strips 102 apart, tensile qualities of the fidget 100 engage receptors of the nervous system and thereby provide the desired proprioceptive, auditory and tactile inputs. Likewise, the alternating alignment of the magnets 102 piques the interest of the user by experiencing proprioceptive input via the "repelling/oppositional" forces. As can be seen in FIG. 12 each of the fabric squares 104 are coupled to at least one other fabric square 104, each having magnets 102 centrally located within fabric squares 104. Each magnet 102 has a corresponding shape with the other magnets 102. FIG. 12 also illustrates that the fabric squares 104 form a linear array of fabric squares, with each of the fabric squares 104 have no more than two other fabric squares 104 adjacent thereto.

Figure 13:
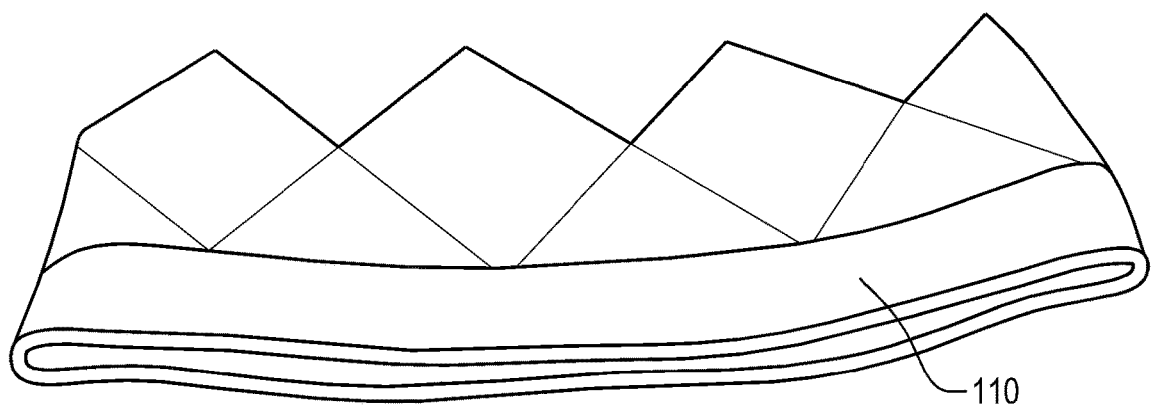
FIG. 13 is a perspective view that illustrates an optional additional accessory of the present invention of in the form of a crown headband.

Also along these lines, FIG. 13 illustrates another inventive accessory in the configuration of a crown headband 110. The crown headband 110 provides selective pressure at a plurality of points around the head, giving the wearer a fitted, compression-like feel. Circumferential input to the area just above the supra-orbital processes provides direct neurological benefits. These benefits can include activation of the body's Labyrinthine righting reflex and proprioceptive balancing. With such neuromuscular re-education, postural alignment can be obtained via activation of the spinal nerves, enhancing the body's capacity for higher cortical learning.

In addition, according to the present invention, there is provided a magnetic book (not shown) that includes a plurality of magnets positioned at a perimeter of a plurality of pages to provide positive intensity resistance, while fostering literacy and functional communication skills. The magnetic book of the present invention may be utilized to provide the user with visual clues to allow the user to participate in their day with greater independence. Visual supports are graphic clues that can be used to aid communication between the caregiver and the patient or user of the book. The inventive magnetic book may also be used as an environmental prompt that aids a child in remembering what is expected of them in a certain activity or routine. The invention may be modified to meet the needs of (1) Social stories in the form of a personalized reference to daily routines and activities, providing comfort and assistance in memory and self-regulation; (2) Visual schedules by laying out the events of a day or routine, one-by-one, and by giving a clear sense of the sequence and expectations of the day; (3) First-Then Boards which show the sequence of events and teach that in order to get a reward the child or patient must sometimes perform a less favorable activity first; and (4) Choice Boards which provide different options of what a child would like to do within activities and routines, thereby helping a user to focus on appropriate options and efficient communication of desires.

Figure 14:
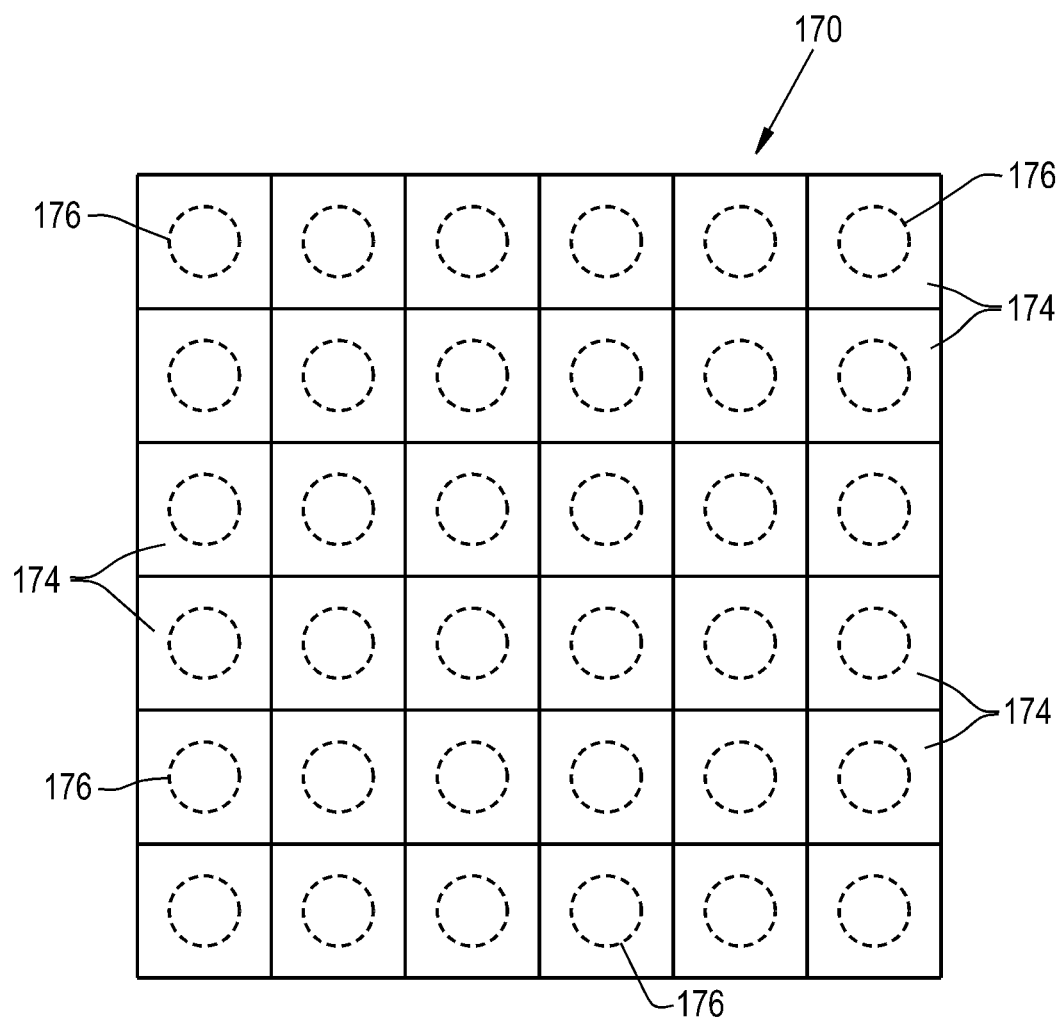
FIG. 14 is a view of another embodiment of a fidget introduced in FIG. 12.

Now, additionally referring to FIG. 14, there is shown another embodiment of the present invention in the form of a weighted blanket 170 that is similar to perimeter blanket 70, but having a complete array of quilted squares 174 each having weighted fillings 176 therein. The weighted fillings 174 are substantially uniformly distributed throughout the fabric shell. Advantageously, since the quilted squares 174 are positioned in the form of an array it allows the user to selectively distribute the weight to provide a desired amount of pressure and tension across selected areas of the body, thereby allowing the user to define the desired proprioceptive input into the nervous system. Blanket 170 provides both weight and compression when draped and/or wrapped about the body with varying degrees of tension. Blanket 170 may further optionally include, encased within the fabric shell, a plurality of magnetic inserts 176 having respective alternating polarities positioned around the periphery of blanket 170 such it may be gathered up into a sack or a bag for a variety of uses.

Figure 15:
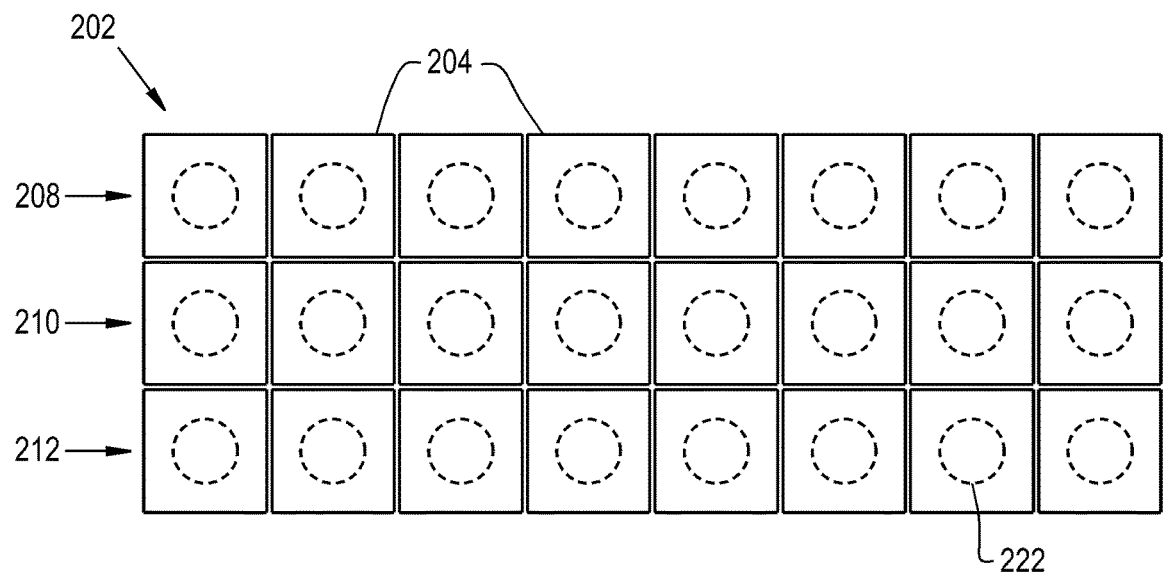
FIG. 15 is a view of an array of elements included in the fidget of FIG. 14.
Figure 16:
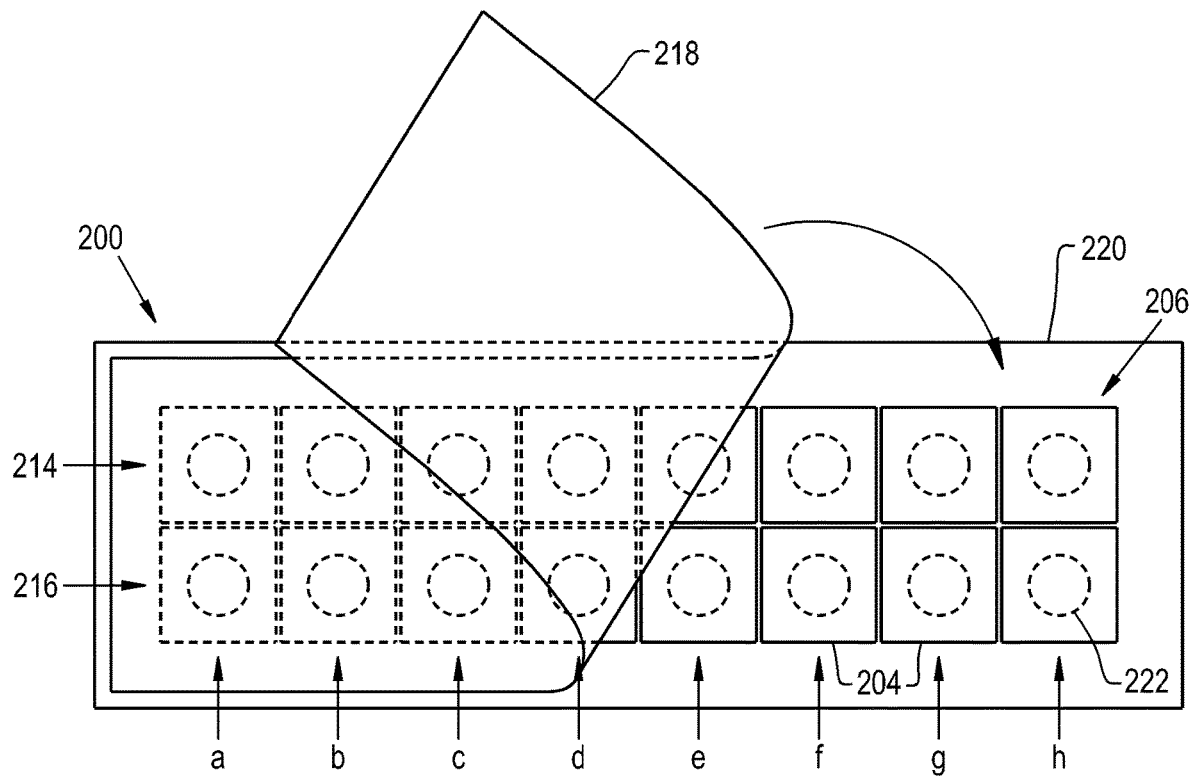
FIG. 16 illustrates a step in the forming of a fidget based on an array of elements, illustrated in FIGS. 14 and 15.

Now, additionally referring to FIGS. 15 and 16 there are shown other variants of the present invention in the form of a layered fabric item 200, where an array 202, of twenty-four filled elements 204, which can include substantially equal amounts of glass or polymer pellets, are shown in FIG. 15 and an array 206 of sixteen filled elements 204 are shown in FIG. 16. Considering the arrangement of FIG. 15, array 202 can be considered to have three linear arrays 208, 210 and 212, each with eight elements 204. In a similar fashion, fabric item 200 can have two linear arrays 214 and 216 that are arranged in array 206. Here fabric item 200 has two outer fabric layers 218 and 220 that are used to enclose array 206. While it is contemplated that elements 204 can be arranged as individual elements that are then positioned and individually secured to fabric layers 218 and 220, it is also considered that linear arrays of elements 204 are manufactured and arranged side-by-side and attached to fabric layers 218 and 220 to form a finished fabric item 200. Fabric layers 218 and 220 are secured to each other and may be secured through array 206 to form a quilted appearance. It is also contemplated that selected seams may be used to secure linear arrays 214 and 216 to layers 218 and 220.

Each filled element 204 can have a weighted filling 222 therein or item 222 can be magnets 222 having magnetic polarities that are arranged for specific purposes. For example, in fabric item 200 (which can also be called a fidget 200), each magnet 222 in linear array 214 can be arranged to have the same or opposing polarities as the immediately adjacent magnet 222. For purposes of explanation each element in linear arrays 214 and 216 are assigned positions a-h therein, and will be referred to as magnet 214a through 216h, and the polarities will be referred to as North (N) facing out of the page or South (S) facing out of the page. One conceived pattern is for magnet 214a to be N and magnet 214b to be S and this alternating pattern continues along linear array 214; and that magnets 216a-h be arranged in a contra pattern of S-N-S-N-S-N-S-N. In this pattern each magnet 222 will be an opposite polarity to its adjacent neighbor. With this arrangement fidget 200 can be folded along the numerous intersections between elements 204 in various ways with the attractive magnetic forces arranging a centering and coupling of each fold. The fidget 200 presents a therapeutic interest for the user, to arrange, rearrange and flip the fidget around to investigate the various ways that it can be arranged, providing physical therapeutic possibilities for the hands, eye-hand coordination exercises and interest to occupy the mind.

Figure 17:
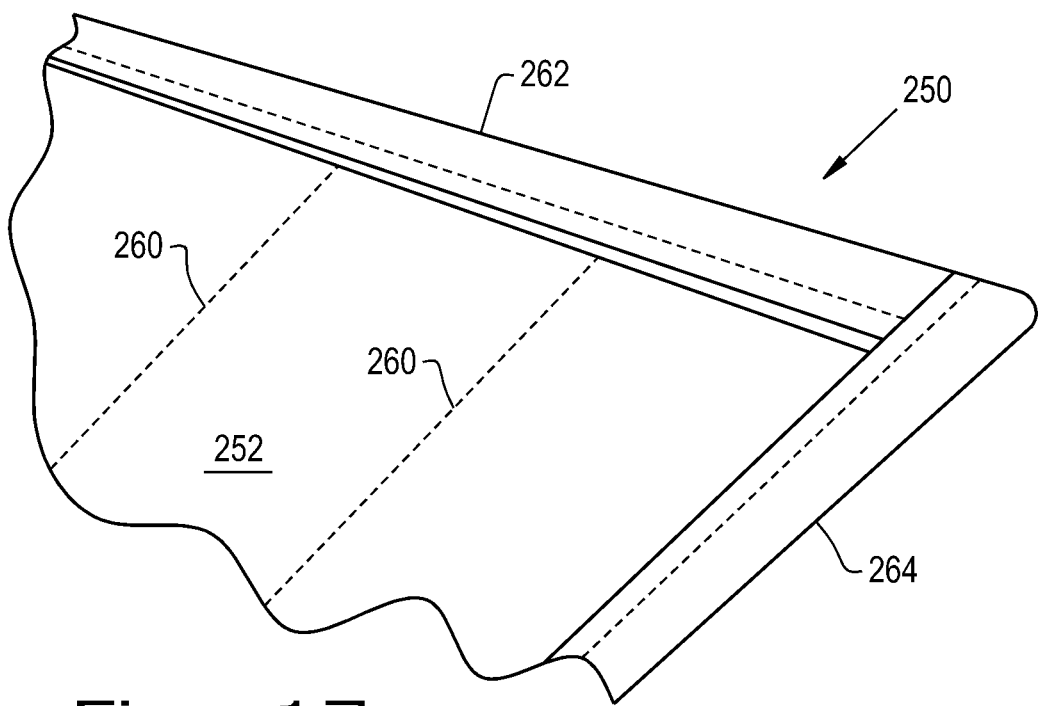
FIG. 17 is a perspective view of an embodiment of the present invention illustrated as a folded blanket having weighted arrays of elements therein.
Figure 18:
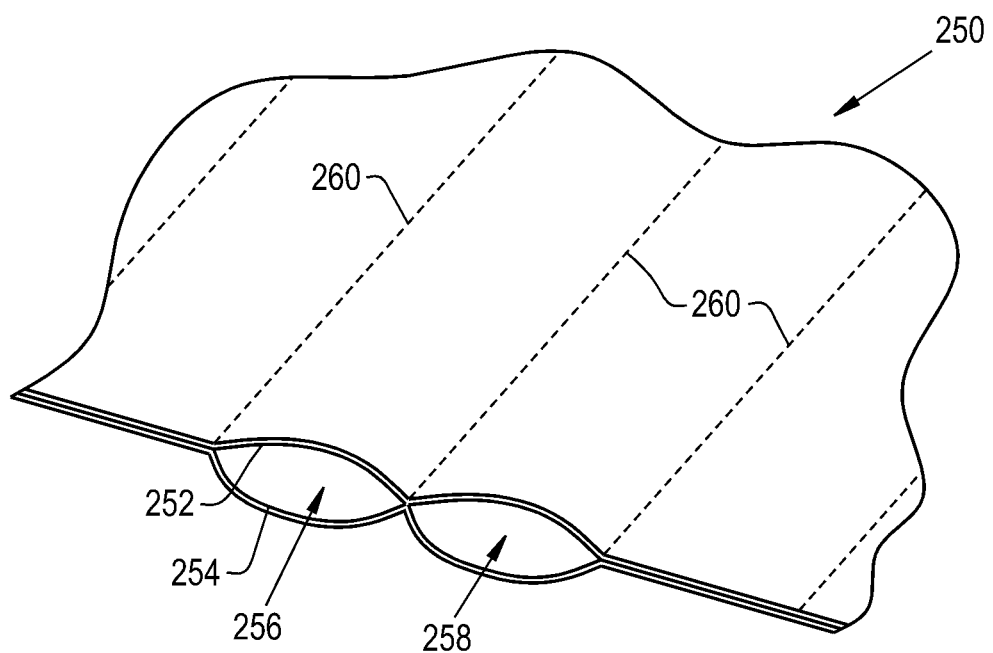
FIG. 18 illustrates open channels in the blanket of FIG. 17.

Now, additionally referring to FIGS. 17 and 18, there is shown yet another embodiment of the present invention in the form of a blanket 250 having outer fabric layers 252 and 254 that are arranged to have channels 256 and 258 formed therein by seams 260 that proceed along a length of blanket 250 with an end seamed piece 262 and a side seamed piece 264 finishing the look of blanket 250. While, for purposes of illustration, two channels 256 and 258 are shown, there are channels all along the width of blanket 250.

Figure 19:
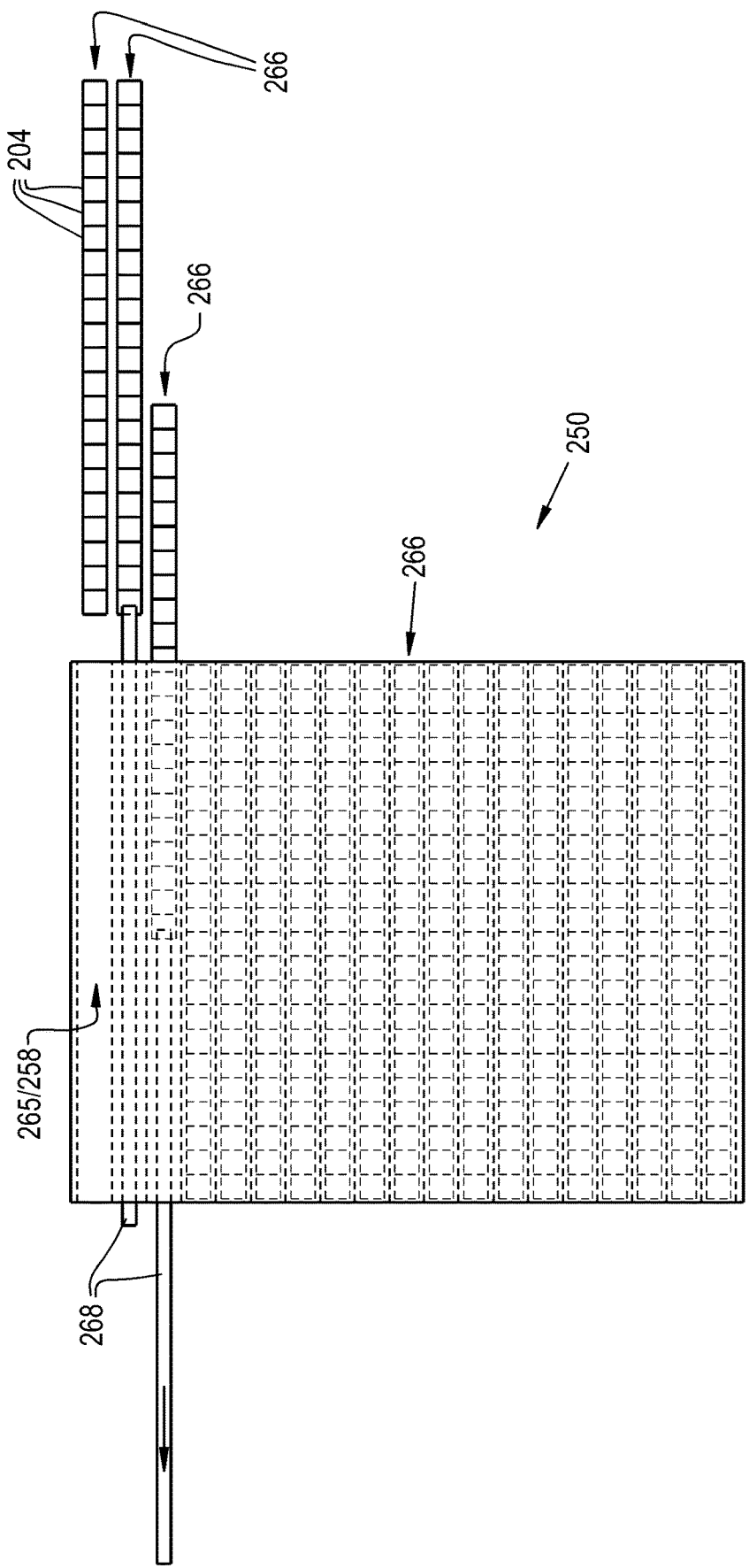
FIG. 19 illustrates the insertion of the weighted arrays of the present invention being inserted into the open channels of the blanket illustrated in FIG. 18.
Figure 20:
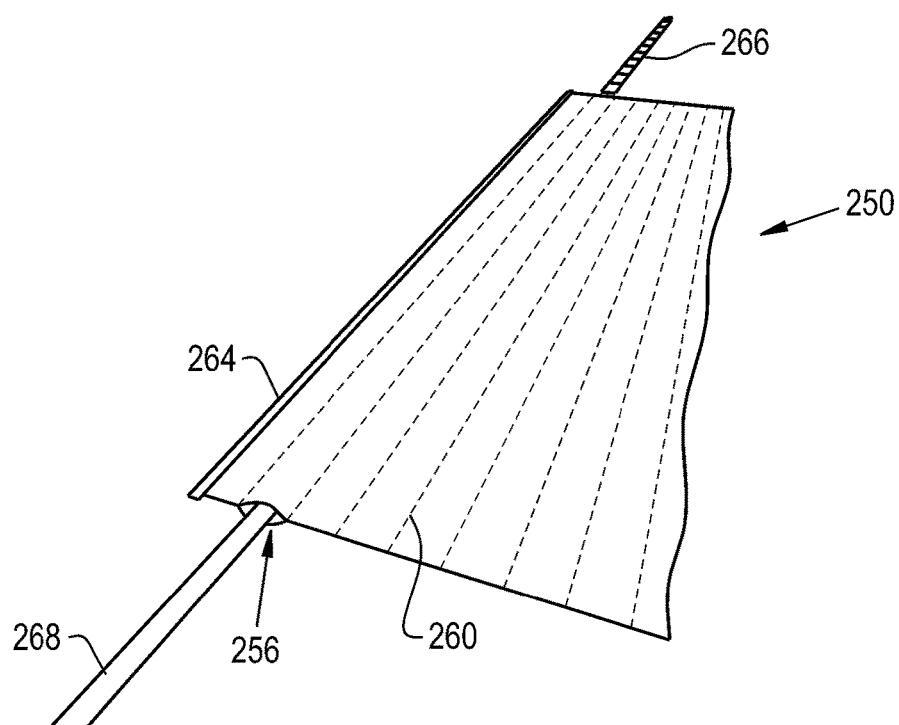
FIG. 20 illustrates the pulling of an array into an open channel of the blanket.
Figure 21:
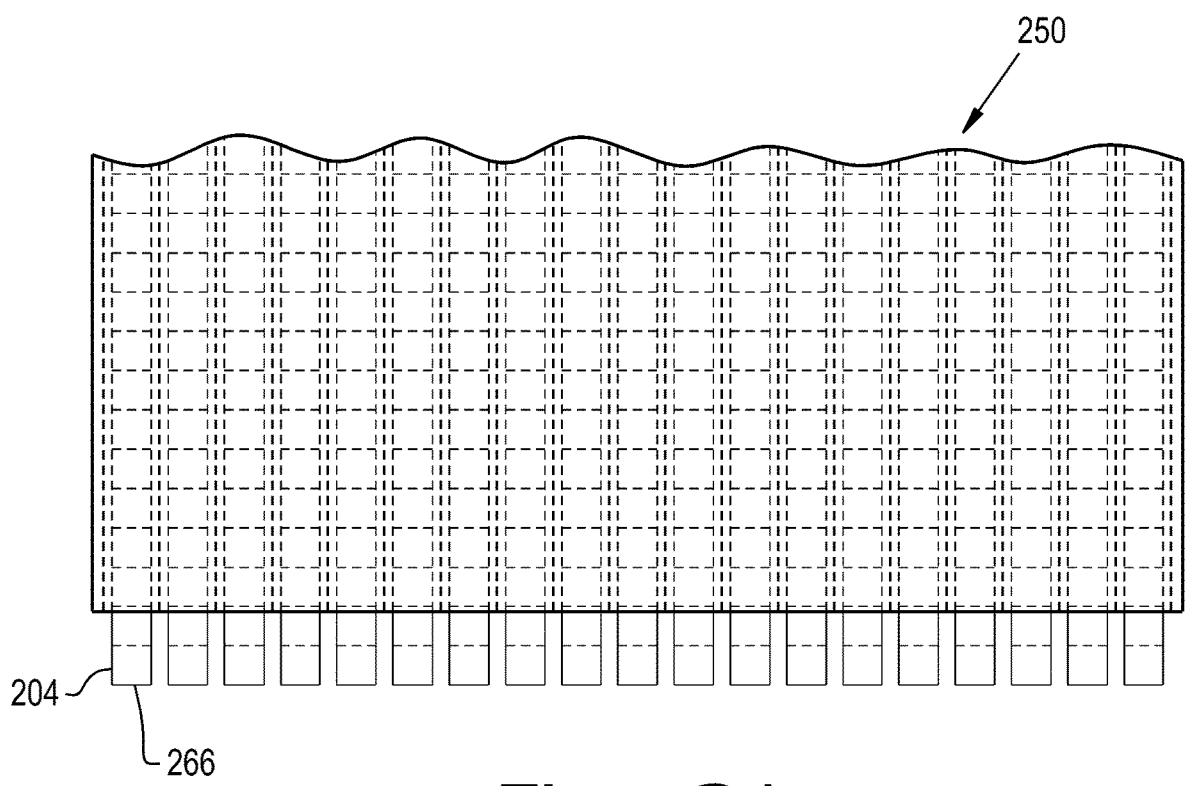
FIG. 21 illustrates the blanket of the present invention with the linear arrays of weighted pockets having been inserted into the channels of the blanket of the present invention.
Figure 22:
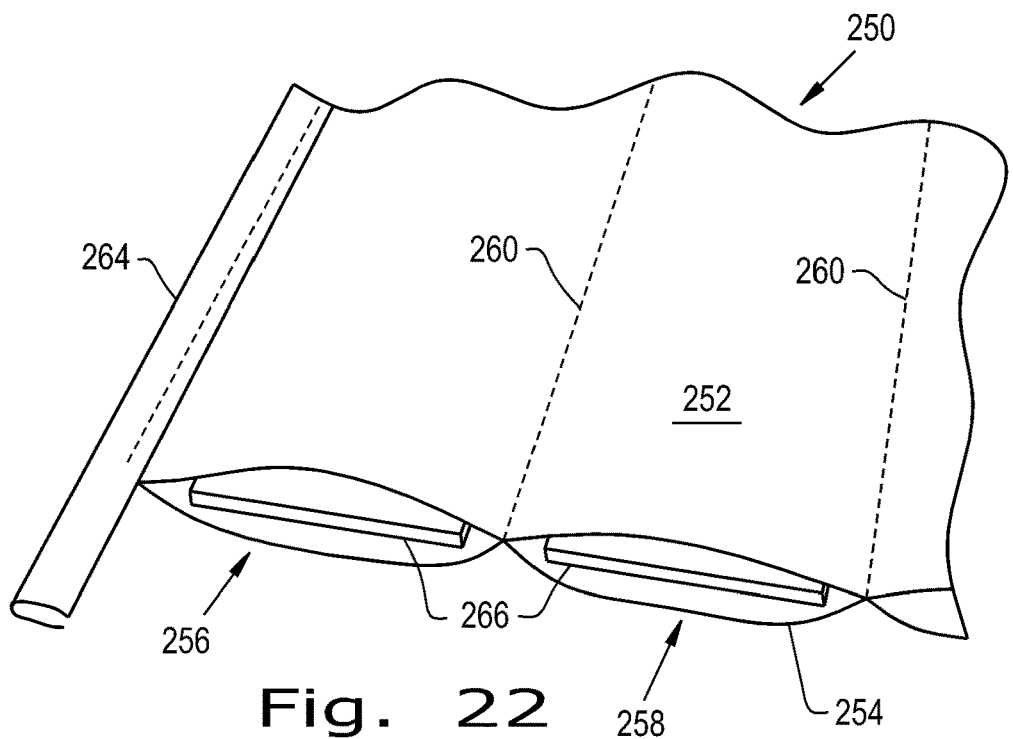
FIG. 22 illustrates a trimmed array and the edges of fabric at an end of an open channel of the blanket illustrated in a previous figure.
Figure 23:
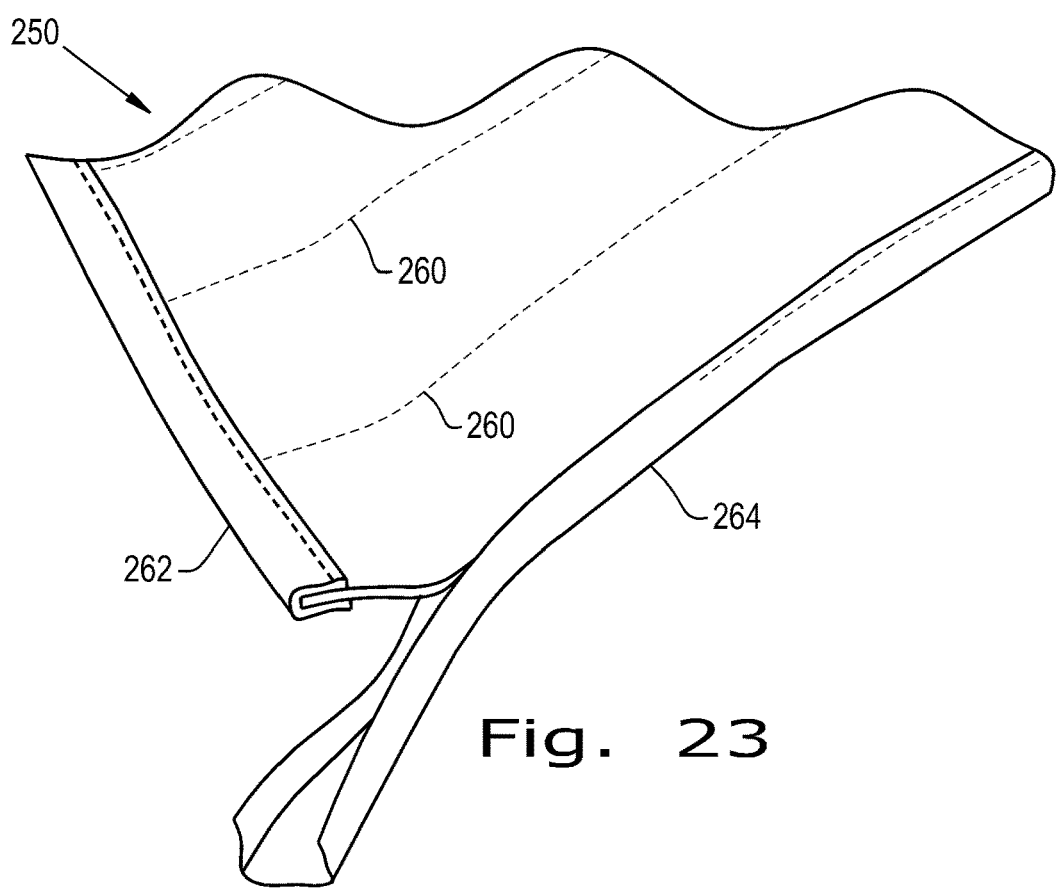
FIG. 23 illustrates the application of edging to the blanket or a garment previously shown.

Now, additionally referring to FIGS. 19-23, there are shown the steps of making blanket 250, as well as the internal structure thereof. Linear arrays 266 of filled elements (weighted sections) 204 are arranged to be pulled into each channel 256/258 using a pulling device 268. Pulling device 268 is a stiffened yet flexible item that is pushed through each channel 256/258 to which each linear array 266 is temporarily coupled and the pulling of device 268 allows each linear array 266 to be positioned in a respective channel, as shown in FIGS. 19 and 20. As shown in FIG. 21 linear arrays 266 have been positioned in each channel of blanket 250, and are arranged so that an end of each linear array 266, as shown in FIG. 22, is positioned at an end of each channel 256/258, so that end piece 262 can be seamed, at each end of channel 256/258, to thereby captivate the ends of each linear array 266 to fabric layers 252 and 254.

Figure 24:
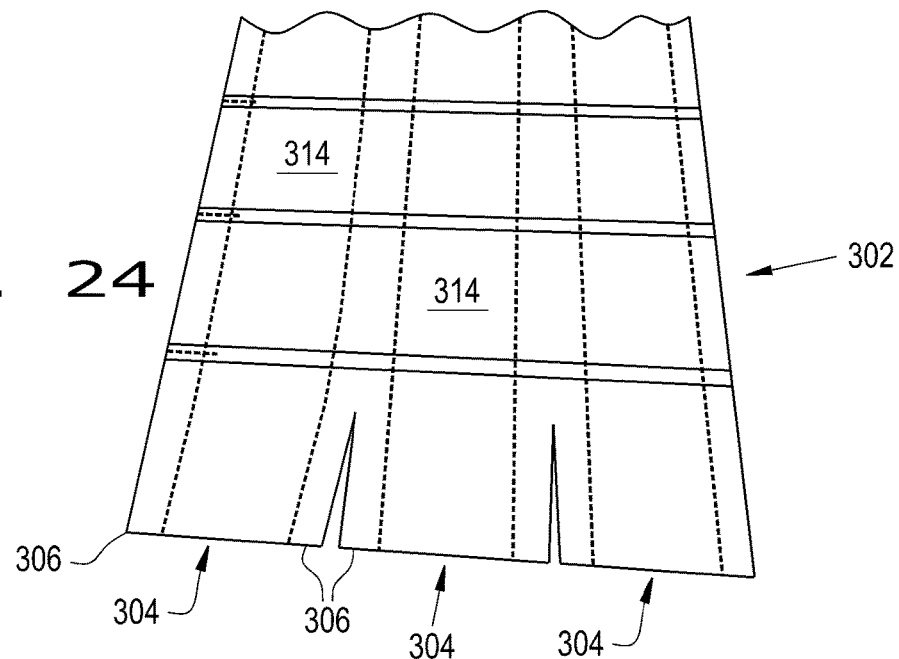
FIG. 24 is a perspective view of another embodiment of the present invention in the form of elements of a therapeutic blanket in the form of three chains having been filled with beads and the three illustrated chains are being cut apart.

Now, additionally referring to FIGS. 24-29, there are shown elements of a therapeutic blanket 300 along with the details of steps taken to make therapeutic blanket 300 of the present invention. Glass beads 320 are added to each square 314 and then square 314 is closed with an ultrasonic weld, not stitching. FIG. 24 illustrates a filling chain group 302 of three chains 304 that are being cut from group 302. Chains 304 are referred to that in this embodiment of the present invention and each square 314 can be considered a link 314 in the linear chain 304. When chains 304 are cut from group 302 approximately one half inch of edge material 306 is left along each side of each chain 304.

Figure 25:
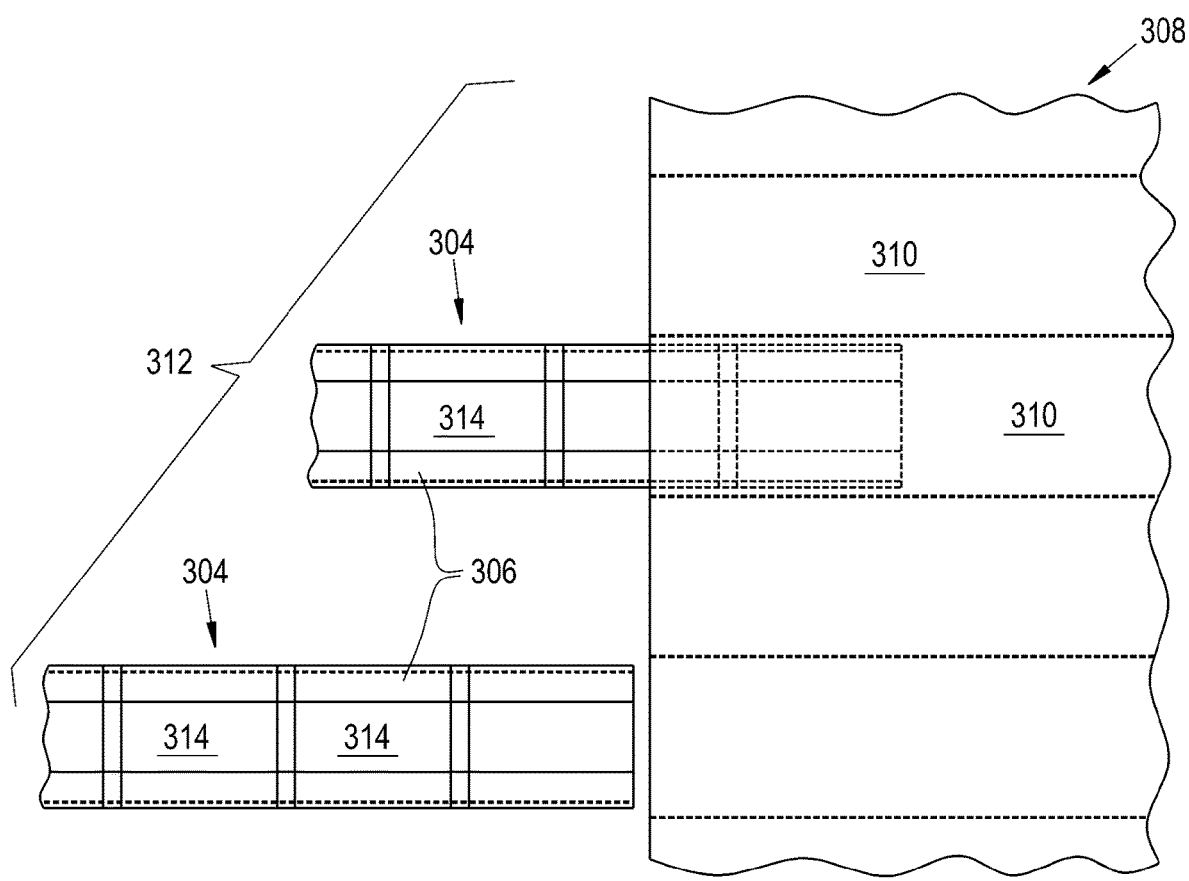
FIG. 25 illustrates the elements of FIG. 24 having been separated, now being inserted into open channels as the therapeutic blanket is being formed.

Edge material 306 is folded onto chain 304 as chain 304 is inserted into a bladder 308, as illustrated in FIG. 25. Bladder 308 has channels 310 that are defined by the space between seams positioned approximately 2 inches apart on two pieces of fabric that are formed into bladder 308. Chains 304 are inserted into channels 310 by first inserting Pull-through Rods into the channels 310 of bladder 308 and an end of each chain 304 is hooked to each pull-through rod. The pull-through rods are then withdrawn thereby pulling chains 304 into channels 310, with edge material 306 being drawn in in a folded over condition. Edge material 306, which can be considered a' inch fold over is important because it helps keep chain 304 in place and not twist around as chain 304 is drawn into channel 310. Further, because of the nature of the medical grade fabric used in blanket 300, the position and folded nature of edge material 306 provides extra cushion in blanket 300. As bladder 308 is filled with chains 304 it becomes a bladder assembly 312.

Figure 26:
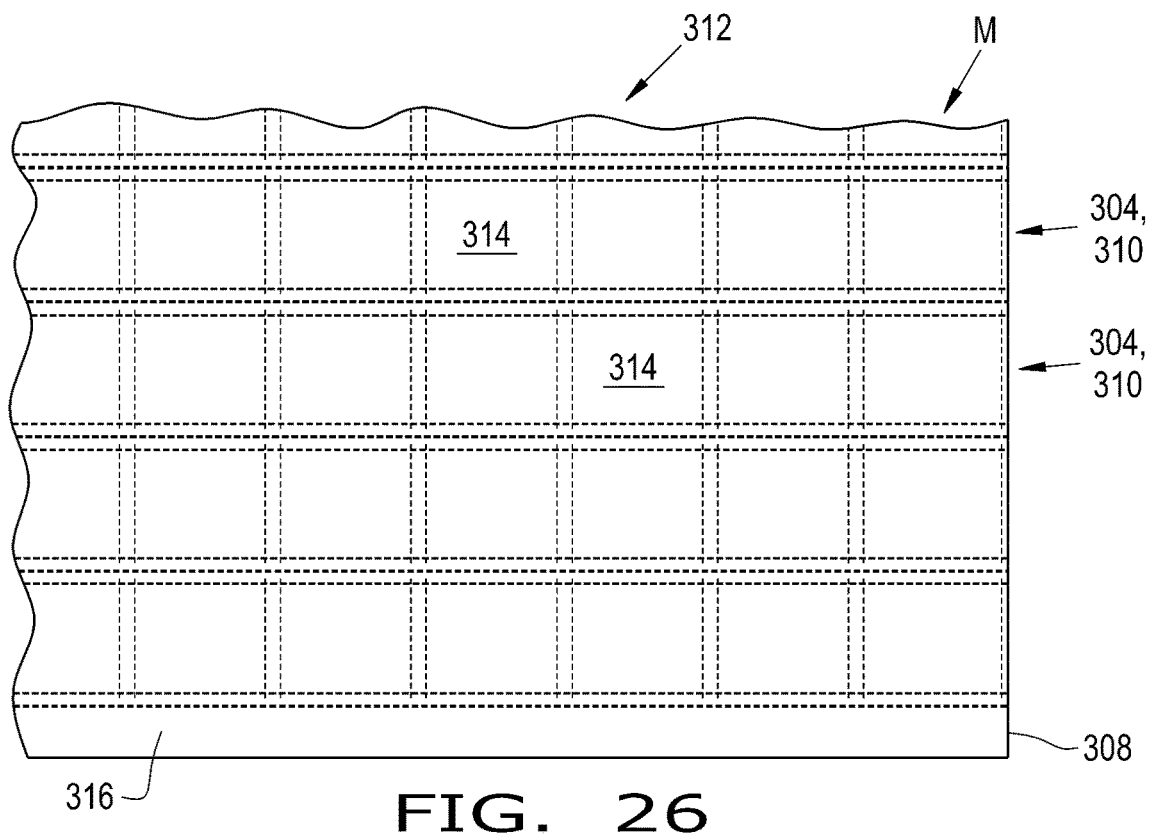
FIG. 26 illustrates the top side of the bladder having the chains of FIG. 24 been inserted.
Figure 27:
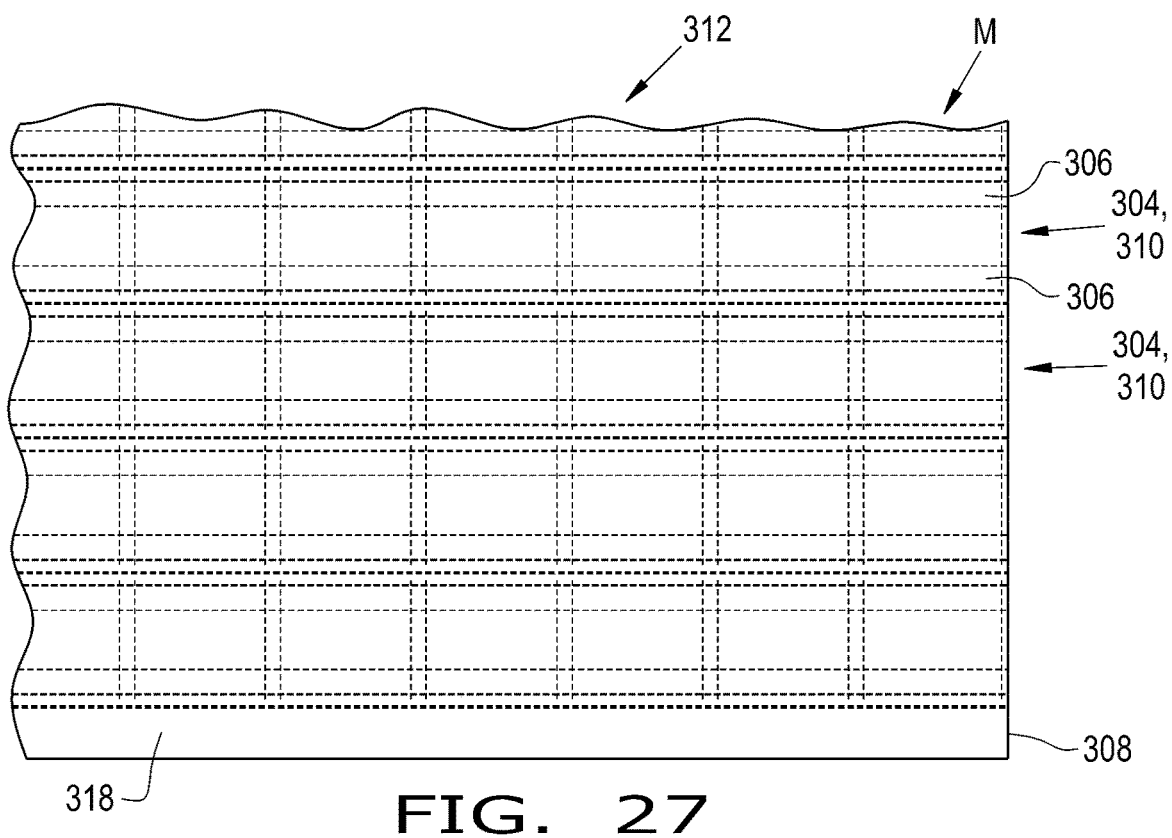
FIG. 27 illustrates the bottom side of the bladder with the edges of the chain being folded over.

Bladder assembly 312 is illustrated with a top view in FIG. 26 and a bottom view FIG. 27. Links 314 form a matrix M of links 314 or cells 314. Chains 304 as well as fabric layers 316 and 318 of bladder 308 may be made of a fabric, such as brushed tricot. At this point in the making of blanket 300, there are 4 layers of brushed tricot (the two layers that form chains 304 and layers 316 and 318+the fold-over edge material 306+the beads 320 in the 2 inch squares 314 with the specific bead weight in each link 314.

Figure 28:
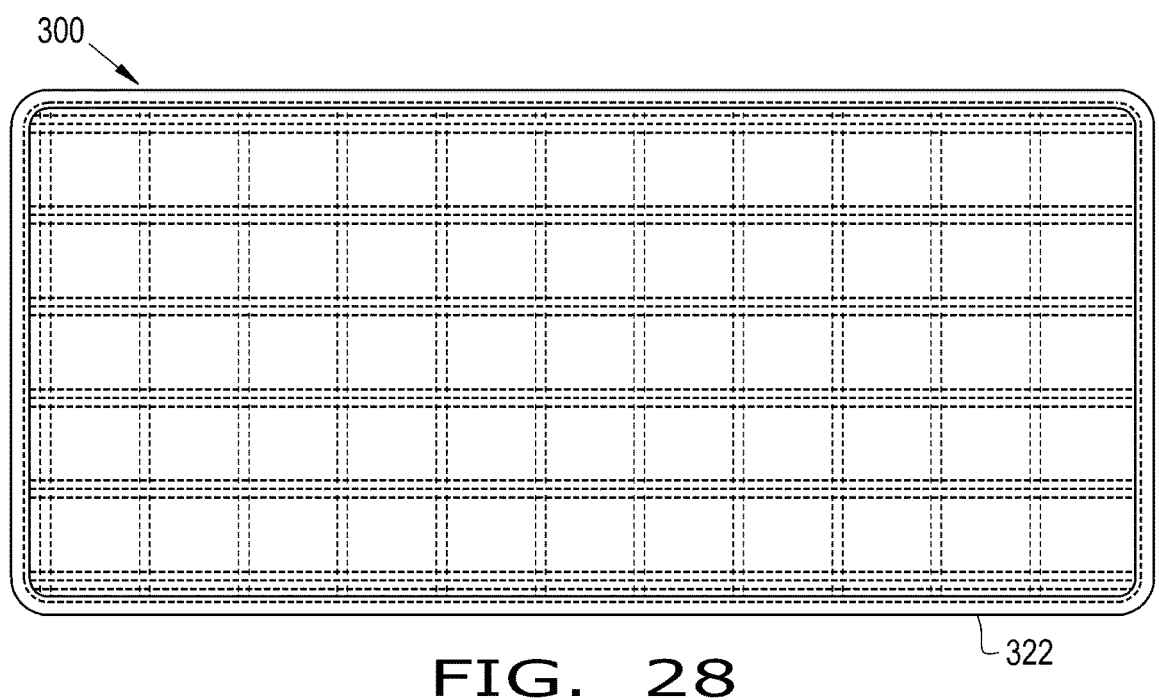
FIG. 28 is a top view of the therapeutic blanket having been formed in FIGS. 24-27.
Figure 29:
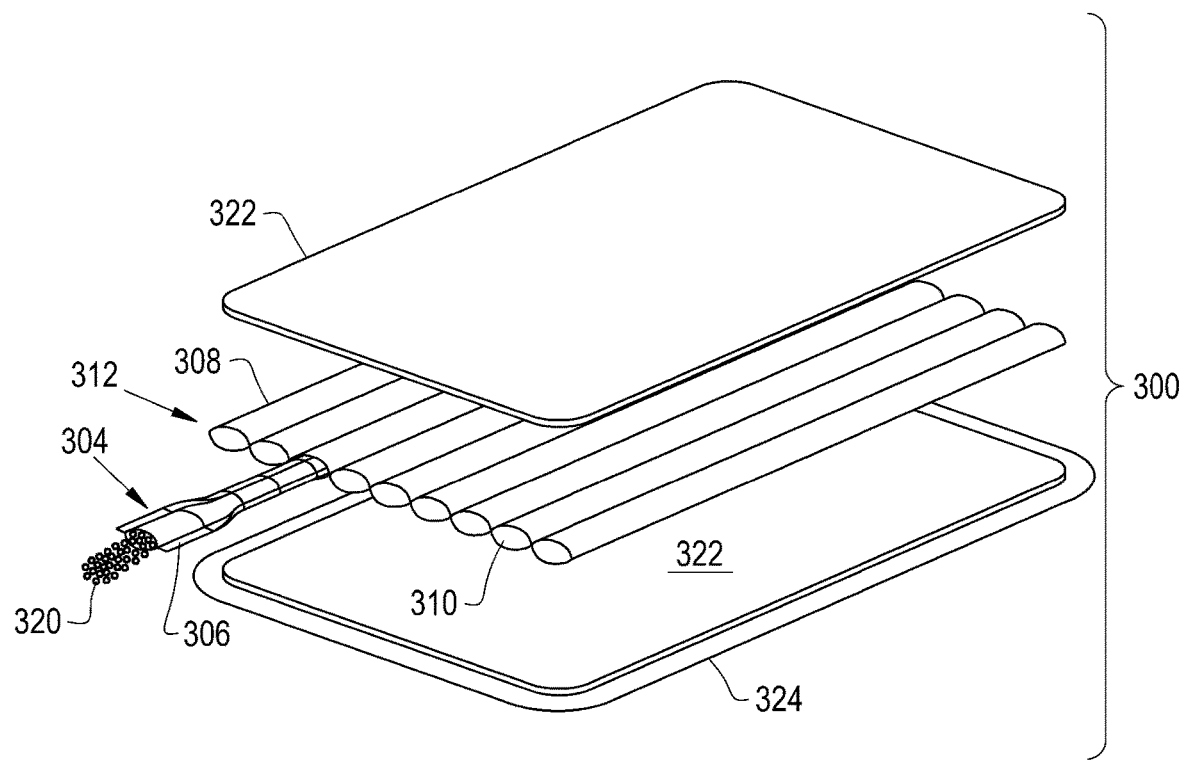
FIG. 29 is an exploded view of the therapeutic blanket of FIG. 28.

Outer shells 322, made of antimicrobial fabric, such as Fusion III fabric are place on both sides of bladder assembly 312 to thereby result in a total of 6 layers of fabric (4 brushed tricot+2 Fusion III). Fabrics 322 and bladder assembly 312 are aligned to prepare for sewing with a baste stitch. It is also contemplated that an ultrasonic welding technique could be used instead of using sewn stitching. Then after a baste stitch is sewn around entire periphery edge, or the perimeter of blanket 300, an overlock stitch is sewn around the perimeter. A binding 324 is then folded over the perimeter and is sewn onto therapeutic blanket 300. Binding 324 can be made of 210 D antimicrobial fabric. As illustrated in FIGS. 28 and 29, blanket 300 has rounded corners. Further, there are no stitches on the main body of the item, so that the product is smooth and able to be wiped clean per the medical protocols in use at hospitals and other medical facilities.

The present invention uses glass beads that are chosen with a specific size of between 2.85 mm and 3.45 mm and are nominally spherical of approximately 3 mm in diameter so that they provide the correct weight in the range of 0.1 Oz. to 0.4 Oz. per 2 inch square, which results in the desired density for each 2" square. Different fill weight selections are generally set at 1, 2, 3 or 4 tenths of an ounce per square of 2 inches to achieve different weights per square inch depending on the size of the item and the needed therapeutic input.

The importance of bead fill with dimensional size products is that it is not just a heavy weight. It is that the placement of weight must be done in the right way with the right amount of weight to promote nerve contact and activation. In other words, the combination of size of square, weight per square inch, size of the bead, and density of bead.

Smaller dimensional size product=less nerve contact area=more weight per square inch to produce Deep Touch Pressure to activate the nerve.

Larger dimensional size product=more nerve contact area=less weight per square inch needed to produce Deep Touch Pressure to activate the nerve.

Purdue Northwest University and Parkview Health System have conducted a study using the present invention. The study was conducted by Jamie Vinson BSN, RN, HN-BC, RYT, the following is mainly the results of that study.

A bedside nurse was inspired to investigate a complementary intervention, historically used to reduce anxiety and agitation in children on the Autism spectrum, for the use of anxiety reduction in adults receiving their first and second outpatient chemotherapy infusions. A research study was conducted that compared the effectiveness of weighted blanket intervention to no blanket intervention in the reduction of anxiety for patients receiving their first two outpatient infusion visits. Anxiety management is often treated with pharmacological measures. This patient-centered innovation gives the patient and nurses a non-pharmacological intervention option to help reduce the patient's anxiety. Comments received from patients about the weighted blanket were overwhelmingly positive. This simple intervention may also lead to an improved patient experience and/or less need for pharmacological interventions for anxiety.

Weighted blankets have been used as a way of delivering Deep Touch Pressure (DTP) to those suffering from autism, ADHD, PTSD, bipolar disorder and insomnia by both occupational therapists and caregivers to help reduce anxiety, increase focus, and promote rest. Weighted blankets have more recently been used to reduce anxiety in painful dental procedures. Some cancer patients experience increased anxiety when receiving chemotherapy infusions. There is a lack of research on the effectiveness of weighted blankets as an intervention for anxiety reduction in patients who are receiving chemotherapy infusions.

A randomized, controlled, crossover study used each patient as their own control to evaluate the effects of weighted blankets on anxiety in outpatient infusion center patients receiving their first and second chemotherapy infusions.

Data collection at admission included: demographics, vital signs, State-Trait Anxiety Inventory for Adults form Y1 (STAIAD-Y1), and Visual Analog Scale (VAS).

Data collection at 30 (+/−5) minutes from when the weighted blanket was placed or from when the admission VAS for anxiety was marked by the patient included: vital signs, STAIAD-Y1, and VAS.

Data collected at patient discharge included: vital signs, VAS and patient/nurse comments.

Inclusion criteria: Cancer patients in the outpatient infusion center receiving their first and second chemotherapy infusions, and Age>18 years of age Exclusion criteria:
Less than 18 years of age
Weight<45 kg
Only receiving one infusion
Currently enrolled in another research study
Diagnosed peripheral neuropathy
Diagnosed fibromyalgia When a weighted blanket was used, patient STAIAD-Y1 scores were reduced by an additional 2.15 (95% CI 4.05, 0.25) on average compared to those where it was not.

Weighted blanket use was associated with a mean 8.89 (95% CI 16.59, 1.18) point additional reduction in VAS scores at the half-hour mark.

The correlation analysis of VAS and STAIAD-Y1 scores showed a strong positive correlation between the two scores.

There were no adverse events with the use of the weighted blanket.

The majority of nurses and patient comments about the weighted blanket were positive.

The Purdue Northwest University and Parkview Health System study found that STAIAD-Y1 and VAS anxiety decreased more with the use of the weighted blanket. The study also concluded that under an adjusted linear mixed-effects model, including STAIAD-Y1 and VAS anxiety, the overall anxiety of the patient also decreased more with the use of the weighted blanket. The study also found that STAIAD-Y1 and VAS anxiety correlate with one another. Therein, a higher STAIAD-Y1 score correlates with a higher VAS anxiety score.

Weighted blankets may be used as a complementary intervention for reducing anxiety in patients receiving chemotherapy.

A standard weight medical-grade therapeutic weighted blanket can be safely used in the adult population.

A visual analog scale is a valid tool to measure anxiety compared to STAIAD-Y1.

Patients and nurses enjoyed using the weighted blanket as an intervention to help reduce anxiety. (end of $1^{st}$ study excerpt).

In a subsequent article the author of the study indicated:

Initially, CapeAble (owner of the present invention) donated three blankets for me to trial in the hospital. Then Amy Poole, director, Oncology Services, asked The HOPE Foundation to donate enough money for us to purchase five medical-grade weighted blankets from CapeAble.

I learned two important things (from the study): 1) These patients experienced a reduction in anxiety through weighted blanket therapy, and 2) You can effectively use the same blanket on patients of all weights. It is not the total weight of the blanket that matters, it is the amount of Deep Touch Pressure (DTP) the blanket delivers (ounces per square inch). This means that there is no need for multiple "weights". We can use a standard weight medical-grade therapeutic weighted blanket for patients of many shapes and sizes. This will change the current guidelines of the weighted blanket industry.

I (received) the American Holistic Nurses Association Research Grant Award this year and have also received funding from the Parkview Foundation. The next step will be to research whether weighted blankets can reduce pre-surgical pain and anxiety, and postsurgical restlessness, nausea and vomiting. Quality Improvement (QI) projects using weighted blankets are also underway here at Parkview. Nurses and patients are seeing amazing results. I am always hearing the testimony of how well the weighted blanket has worked in all sorts of scenarios. I would like to be the first hospital to implement weighted blankets as a standard of care for all patients in the health system. (end of excerpt).

In a recent study ($2^{nd}$ study herein) of the therapeutic blanket of the present invention carried out by Hannah Rawlinson, she stated that—Application of a CapeAble (owner of the present invention) weighted blanket to create DTP to improve quality of sleep. CapeAble weighted blankets were donated for the use of this project. The focus is on neuroscience and neurological response to maximize complete nerve contact through the weighted blanket (Pacheco, 2018). The blankets are unique in their structure, providing evenly distributed weight over the entire body. The difference in CapeAble weighted blankets compared to weighted blankets that have been used over the past 30 years is their ability to use less weight more effectively. These medical grade blankets are designed with 0.20 ounces per two-inch square pocket of glass beads (Pacheco, 2018). This design does not allow for the weight within the blanket to shift. When the blankets are applied to patients, the blanket is able to conform to any shape or size body. The blanket compresses evenly and stays in direct contact with the patient's nerves. By stimulating the ANS through DTP, it signals the brain to release calming chemicals and endorphins (Pacheco, 2018). CapeAble weighted blankets are easily manipulatable and gentle on the patients. Medical grade CapeAble weighted blankets come in three sizes; small, medium, and [twin]. Blanket size is chosen based on age, size, frailty, and diagnosis. (end of $2^{nd}$ study excerpt).

The present invention is a therapeutic blanket 300 and includes first and second outer layers 322 that are attached together. An internal matrix M of generally equal sized cells 314 lies between layers 322. Each cell 314 containing a measured weighted mass 320, the mass 320 being held within the respective cell 314. The matrix M is secured to the first and second outer layers 322 along an outer perimeter binding 324 of blanket 300. As illustrated, matrix M is only secured along the outer perimeter and is not otherwise attached to layers 322. The mass of each measured weighted mass is substantially similar, and matrix M extends substantially to the outer perimeter of the first and second outer layers 322. The mass of each measured weighted mass 320 is within the range of 0.1-0.4 Oz. with the preferred fill being approximately 0.2 Oz.

Each cell 314 is approximately four square inches in area, with the width and length that are approximately equal, of approximately 2 inches. Each cell 314 of chain 304 of matrix M is configured to be sequentially sealed after a preselected amount of the weighted mass 320 that includes glass or polymer pellets 320 is inserted therein.

First outer layer and the second outer layer 322 is an anti-microbial fabric. The matrix M is a bladder assembly 312 that includes a series of weighted chains 304 pulled into channels 310 of a bladder 308. Weighted chains 304 have an edge material 306 that is folded over on each chain 304 within the channel 310 in which the chain 304 is placed.

Another way of considering therapeutic blanket 300 is that it includes a plurality of weighted fabric chains 304, a bladder 308 having a plurality of channels 310 therein. A corresponding one of the fabric chains 304 are inserted into each of the channels 310. Top fabric layer 322, bottom fabric layer 322, and the bladder 308 are secured together. The bladder 308 being between the top fabric layer 322 and the bottom fabric layer 322 along an outer perimeter 324 of fabric layers 322.

Each of the plurality of chains 304 have a portion 306 along the length of the chain 304 that is folded over as chain 304 is inserted into the associated channel 310. Each chain 304 is secured to bladder 308 and bladder 308 is secured to fabric layers 322 along perimeter 324 of fabric layers 322.

While this invention has been described with respect to at least one embodiment, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains.

What is claimed is:

1. A therapeutic blanket, comprising:
a first outer layer;
a second outer layer attached to the first outer layer; and
an internal matrix of generally equal sized cells, each cell containing a measured weighted mass, the mass being held within the respective cell, the matrix being secured to the first and second outer layers along an outer perimeter of the blanket, the matrix being a bladder assembly including a bladder having a plurality of channels therein and a plurality of weighted fabric chains, each of the plurality of fabric chains being respectively inserted into each of the plurality of channels of the bladder, each of the plurality of fabric chains having a first edge material and a second edge material being respectively folded over onto each chain.

2. The therapeutic blanket of claim 1, wherein the mass of each measured weighted mass is substantially similar and is in the range of 0.1-0.4 Oz.

3. The therapeutic blanket of claim 2, wherein the matrix extends substantially to the outer perimeter of the first and second outer layers.

4. The therapeutic blanket of claim 2, wherein the mass of each measured weighted mass is approximately 0.2 Oz.

5. The therapeutic blanket of claim 4, wherein each cell is approximately four square inches in area.

6. The therapeutic blanket of claim 5, wherein each cell has a width and a length that are approximately equal.

7. The therapeutic blanket of claim 6, wherein the width and the length are approximately 2 inches.

8. The therapeutic blanket of claim 7, wherein each cell of the matrix is configured to be sequentially sealed after a preselected amount of the weighted mass that includes glass or polymer pellets is inserted therein.

9. The therapeutic blanket of claim 1, wherein at least one of the first outer layer and the second outer layer is an anti-microbial fabric.

10. A therapeutic blanket, comprising:
   a plurality of weighted fabric chains, each of the plurality of fabric chains having a first edge material and a second edge material being respectively folded over onto each chain;
   a bladder having a plurality of channels therein, a corresponding one of the fabric chains being inserted into each of the channels;
   a top fabric layer; and
   a bottom fabric layer, the bladder being secured between the top fabric layer and the bottom fabric layer along an outer perimeter of the fabric layers.

11. The therapeutic blanket of claim 10, wherein each of the chains have a plurality of links, each of the links in the fabric chains are substantially similar in size and each of the links contain a mass of beads that are substantially similar and is in the range of 0.1-0.4 Oz.

12. The therapeutic blanket of claim 11, wherein the chains have ends that extend substantially to the outer perimeter of the top and bottom fabric layers.

13. The therapeutic blanket of claim 11, wherein the mass of the beads in each link is approximately 0.2 Oz.

14. The therapeutic blanket of claim 13, wherein each link is approximately four square inches in area.

15. The therapeutic blanket of claim 14, wherein each link has a width and a length that are approximately equal and the length and width are approximately 2 inches.

16. The therapeutic blanket of claim 15, wherein each link of each fabric chain is configured to be sequentially sealed after a preselected mass that includes glass or polymer beads are inserted therein.

17. The therapeutic blanket of claim 10, wherein each fabric chain is secured to the bladder and the bladder is secured to the top fabric layer and the bottom fabric layer along a perimeter of the top fabric layer and the bottom fabric layer.

* * * * *

UNITED STATES PATENT AND TRADEMARK OFFICE
CERTIFICATE OF CORRECTION

Page 1 of 1

PATENT NO. : 10,974,018 B2
APPLICATION NO. : 16/845545
DATED : April 13, 2021
INVENTOR(S) : Marna G. Pacheco It is certified that error appears in the above-identified patent and that said Letters Patent is hereby corrected as shown below:

In the Specification

Column 10
At Line 59, please delete "a' inch fold" and substitute therefore --a ½ inch fold--.

Signed and Sealed this
Twenty-eighth Day of February, 2023

Katherine Kelly Vidal
*Director of the United States Patent and Trademark Office*